United States Patent
Di Clemente et al.

(10) Patent No.: US 9,856,307 B2
(45) Date of Patent: Jan. 2, 2018

(54) SOLUBLE MONOMERIC ANTI-MULLERIAN HORMONE RECEPTOR TYPE II FUSION PROTEINS AND USES THEREOF

(71) Applicants: INSERM (INSTITUT NATIONAL DE LA SANTÉ ET DE LA RECHERCHE MÉDICALE), Paris (FR); UNIVERSITÉ PARIS—SUD, Orsay (FR)

(72) Inventors: Nathalie Di Clemente, Paris (FR); Richard Cate, Paris (FR)

(73) Assignees: INSERM (INSTITUT NATIONAL DE LA SANTÉ ET DE LA RECHERCHE MÉDICALE), Paris (FR); UNIVERSITÉ PARIS—SUD, Orsay (FR)

( * ) Notice: Subject to any disclaimer, the term of this patent is extended or adjusted under 35 U.S.C. 154(b) by 0 days.

(21) Appl. No.: 15/115,969

(22) PCT Filed: Feb. 2, 2015

(86) PCT No.: PCT/EP2015/052075
§ 371 (c)(1),
(2) Date: Aug. 2, 2016

(87) PCT Pub. No.: WO2015/114142
PCT Pub. Date: Aug. 6, 2015

(65) Prior Publication Data
US 2017/0166625 A1 Jun. 15, 2017

(30) Foreign Application Priority Data
Feb. 3, 2014 (EP) ..................... 14153715

(51) Int. Cl.
*G01N 33/68* (2006.01)
*G01N 33/574* (2006.01)
*G01N 33/74* (2006.01)
*C07K 14/72* (2006.01)
*A61K 38/00* (2006.01)

(52) U.S. Cl.
CPC ....... *C07K 14/72* (2013.01); *G01N 33/57488* (2013.01); *G01N 33/689* (2013.01); *G01N 33/74* (2013.01); *A61K 38/00* (2013.01); *C07K 2319/30* (2013.01); *G01N 2333/575* (2013.01); *G01N 2333/72* (2013.01); *G01N 2800/367* (2013.01)

(58) Field of Classification Search
CPC ............. C07K 14/72; G01N 33/57488; G01N 33/689; G01N 33/74; G01N 2800/367; A61K 38/00
See application file for complete search history.

(56) References Cited

FOREIGN PATENT DOCUMENTS

| WO | 95-16709 A2 | 6/1995 |
|---|---|---|
| WO | 2011-045202 A1 | 4/2011 |

OTHER PUBLICATIONS

Nathalie Di Clemente et al: "Processing of Anti-Müllerian Hormone Regulates Receptor Activation by a Mechanism Distinct from TGF-[beta]", Molecular Endocrinology, vol. 24, No. 11, Nov. 1, 2010, pp. 2193-2206.

Yuan Qinq-An et al: "Development of engineered antibodies specific for the Mullerian inhibiting substance type II receptor: a promising candidate for targeted therapy of ovarian cancer", Molecular Cancer Therapeutics, vol. 5, No. 8, Aug. 2008, pp. 2096-2105.

Di Clemente et al: "Anti-Mullerian hormone receptor defect", Bailliere's Best Practice and Research. Clinical Endocrinologyand Metabolism, Bailliere Tindall, London, GB, vol. 20, No. 4, Dec. 8, 2006, pp. 599-610.

*Primary Examiner* — Daniel C Gamett
(74) *Attorney, Agent, or Firm* — Witham, Curtis & Cook, P.C.

(57) ABSTRACT

The present invention relates to soluble monomeric Anti-Mullerian Hormone Receptor type II (AMHRII) fusion proteins and uses thereof, in particular for detection or quantification of the bioactive cleaved form of Anti-Müllerian Hormone in a sample. In particular, the present invention relates to a soluble monomeric AMHRII fusion protein wherein one AMHRII extracellular domain is fused to a heterologous polypeptide. A further aspect of the present invention relates to a method for detecting or quantifying the presence of bioactive cleaved AMH in a sample, said method comprising contacting the sample with a soluble monomeric AMHRII fusion protein of the invention.

22 Claims, 12 Drawing Sheets

Co-express AMHRII-Fc and Fc cDNAs in 293E cells

SEQUENCE LISTING

```
<160> NUMBER OF SEQ ID NOS: 2

<210> SEQ ID NO 1
<211> LENGTH: 573
<212> TYPE: PRT
<213> ORGANISM: Homo sapiens
```

<400> SEQUENCE: 1

Met Leu Gly Ser Leu Gly Leu Trp Ala Leu Leu Pro Thr Ala Val Glu
1               5                   10                  15

Ala Pro Pro Asn Arg Arg Thr Cys Val Phe Glu Ala Pro Gly Val
            20                  25                  30

Arg Gly Ser Thr Lys Thr Leu Gly Glu Leu Leu Asp Thr Gly Thr Glu
        35                  40                  45

Leu Pro Arg Ala Ile Arg Cys Leu Tyr Ser Arg Cys Cys Phe Gly Ile
    50                  55                  60

Trp Asn Leu Thr Gln Asp Arg Ala Gln Val Glu Met Gln Gly Cys Arg
65                  70                  75                  80

Asp Ser Asp Glu Pro Gly Cys Glu Ser Leu His Cys Asp Pro Ser Pro
                85                  90                  95

Arg Ala His Pro Ser Pro Gly Ser Thr Leu Phe Thr Cys Ser Cys Gly
            100                 105                 110

Thr Asp Phe Cys Asn Ala Asn Tyr Ser His Leu Pro Pro Gly Ser
        115                 120                 125

Pro Gly Thr Pro Gly Ser Gln Gly Pro Gln Ala Ala Pro Gly Glu Ser
    130                 135                 140

Ile Trp Met Ala Leu Val Leu Leu Gly Leu Phe Leu Leu Leu Leu
145                 150                 155                 160

Leu Leu Gly Ser Ile Ile Leu Ala Leu Leu Gln Arg Lys Asn Tyr Arg
                165                 170                 175

Val Arg Gly Glu Pro Val Pro Glu Pro Arg Pro Asp Ser Gly Arg Asp
            180                 185                 190

Trp Ser Val Glu Leu Gln Glu Leu Pro Glu Leu Cys Phe Ser Gln Val
        195                 200                 205

Ile Arg Glu Gly Gly His Ala Val Val Trp Ala Gly Gln Leu Gln Gly
    210                 215                 220

Lys Leu Val Ala Ile Lys Ala Phe Pro Pro Arg Ser Val Ala Gln Phe
225                 230                 235                 240

Gln Ala Glu Arg Ala Leu Tyr Glu Leu Pro Gly Leu Gln His Asp His
                245                 250                 255

Ile Val Arg Phe Ile Thr Ala Ser Arg Gly Gly Pro Gly Arg Leu Leu
            260                 265                 270

Ser Gly Pro Leu Leu Val Leu Glu Leu His Pro Lys Gly Ser Leu Cys
        275                 280                 285

His Tyr Leu Thr Gln Tyr Thr Ser Asp Trp Gly Ser Ser Leu Arg Met
    290                 295                 300

Ala Leu Ser Leu Ala Gln Gly Leu Ala Phe Leu His Glu Glu Arg Trp
305                 310                 315                 320

Gln Asn Gly Gln Tyr Lys Pro Gly Ile Ala His Arg Asp Leu Ser Ser
                325                 330                 335

Gln Asn Val Leu Ile Arg Glu Asp Gly Ser Cys Ala Ile Gly Asp Leu
            340                 345                 350

Gly Leu Ala Leu Val Leu Pro Gly Leu Thr Gln Pro Pro Ala Trp Thr
        355                 360                 365

Pro Thr Gln Pro Gln Gly Pro Ala Ala Ile Met Glu Ala Gly Thr Gln
    370                 375                 380

Arg Tyr Met Ala Pro Glu Leu Leu Asp Lys Thr Leu Asp Leu Gln Asp
385                 390                 395                 400

Trp Gly Met Ala Leu Arg Arg Ala Asp Ile Tyr Ser Leu Ala Leu Leu

```
                405                 410                 415
Leu Trp Glu Ile Leu Ser Arg Cys Pro Asp Leu Arg Pro Asp Ser Ser
            420                 425                 430

Pro Pro Pro Phe Gln Leu Ala Tyr Glu Ala Glu Leu Gly Asn Thr Pro
        435                 440                 445

Thr Ser Asp Glu Leu Trp Ala Leu Ala Val Gln Glu Arg Arg Arg Pro
    450                 455                 460

Tyr Ile Pro Ser Thr Trp Arg Cys Phe Ala Thr Asp Pro Asp Gly Leu
465                 470                 475                 480

Arg Glu Leu Leu Glu Asp Cys Trp Asp Ala Asp Pro Glu Ala Arg Leu
                485                 490                 495

Thr Ala Glu Cys Val Gln Gln Arg Leu Ala Ala Leu Ala His Pro Gln
            500                 505                 510

Glu Ser His Pro Phe Pro Glu Ser Cys Pro Arg Gly Cys Pro Pro Leu
        515                 520                 525

Cys Pro Glu Asp Cys Thr Ser Ile Pro Ala Pro Thr Ile Leu Pro Cys
    530                 535                 540

Arg Pro Gln Arg Ser Ala Cys His Phe Ser Val Gln Gln Gly Pro Cys
545                 550                 555                 560

Ser Arg Asn Pro Gln Pro Ala Cys Thr Leu Ser Pro Val
                565                 570

<210> SEQ ID NO 2
<211> LENGTH: 330
<212> TYPE: PRT
<213> ORGANISM: Homo sapiens

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

-continued

```
Lys Ala Leu Pro Ala Pro Ile Glu Lys Thr Ile Ser Lys Ala Lys Gly
    210             215                 220
Gln Pro Arg Glu Pro Gln Val Tyr Thr Leu Pro Pro Ser Arg Asp Glu
225             230                 235             240
Leu Thr Lys Asn Gln Val Ser Leu Thr Cys Leu Val Lys Gly Phe Tyr
            245                 250                 255
Pro Ser Asp Ile Ala Val Glu Trp Glu Ser Asn Gly Gln Pro Glu Asn
            260             265                 270
Asn Tyr Lys Thr Thr Pro Pro Val Leu Asp Ser Asp Gly Ser Phe Phe
        275             280                 285
Leu Tyr Ser Lys Leu Thr Val Asp Lys Ser Arg Trp Gln Gln Gly Asn
    290             295                 300
Val Phe Ser Cys Ser Val Met His Glu Ala Leu His Asn His Tyr Thr
305             310             315                 320
Gln Lys Ser Leu Ser Leu Ser Pro Gly Lys
            325             330
```

SOLUBLE MONOMERIC ANTI-MULLERIAN HORMONE RECEPTOR TYPE II FUSION PROTEINS AND USES THEREOF

FIELD OF THE INVENTION

The present invention relates to soluble monomeric Anti-Mullerian Hormone Receptor type II (AMHRII) fusion proteins and uses thereof, in particular for detection or quantification of the bioactive cleaved form of Anti-Müllerian Hormone in a sample.

BACKGROUND OF THE INVENTION

Figure 1:
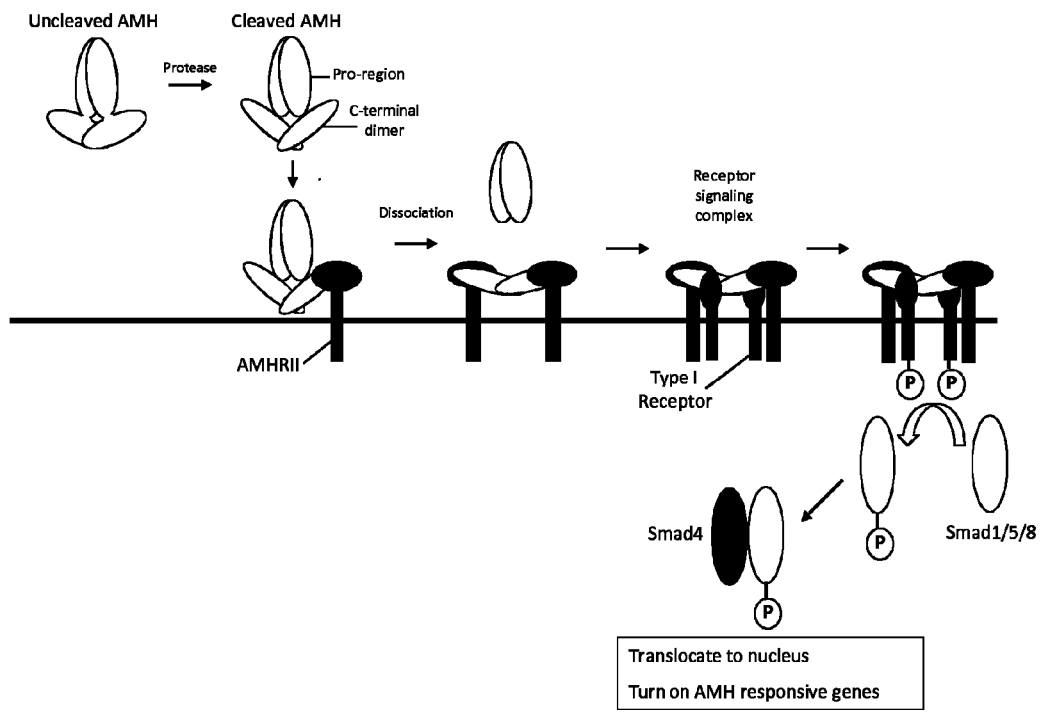

Anti-Mullerian Hormone (AMH), a member of the Transforming Growth Factor (TGF)-beta family, has important roles in normal male and female reproductive development [1]. In addition, AMH has clinical applications in reproductive endocrinology and potentially oncology, which has focused attention on the AMH signal transduction pathway, with the goal of identifying new approaches for therapeutic intervention and diagnostics [2,3]. Like other members of the TGF-beta family, AMH signals by assembling a transmembrane serine/threonine kinase receptor complex of type I and type II components, resulting in the phosphorylation and activation of type I receptor kinase by the constitutively active kinase domain of the type II receptor. The activated type I receptor then phosphorylates the cytoplasmic Smad proteins 1, 5, or 8, which migrate into the nucleus and, in concert with other transcription factors, regulate responsive genes [4,5]. AMHRII, the type II receptor, and AMH, are mutually specific, while ALKs 2, 3 and 6 serve as type I receptors for both AMH and members of the Bone Morphogenetic Protein (BMP) family [6,7]. AMH is translated as a homodimeric precursor, containing an N-terminal pro-region and a smaller C-terminal mature domain. The precursor undergoes an obligatory cleavage at monobasic sites between the two domains, but the pro-region and C-terminal homodimers remain associated in a noncovalent complex. Unlike other TGF-β ligands, the noncovalent complex can bind to AMHRII, which induces dissociation of the pro-region [8]. A similar mechanism has been proposed for the BMP-7 noncovalent complex [9]. A model is presented in FIG. 1, showing processing of AMH, assembly of the AMH receptor signaling complex, and intracellular signaling.

In the male vertebrate embryo, AMH is responsible for the regression of Mullerian ducts, the anlagen of the uterus, Fallopian tubes, and upper part of the vagina. In the adult male, AMH plays a role in Leydig cell differentiation and function [10]. In females, the role of AMH has been predominantly elucidated in rodents, where it has been shown to have an inhibitory effect on primordial follicle recruitment as well as on the responsiveness of growing follicles to Follicle-Stimulating Hormone (FSH) [11,12]. AMH is expressed in Sertoli cells of the fetal and postnatal testis and granulosa cells of the postnatal ovary, whereas AMHRII is expressed in the mesenchymal cells surrounding the Mullerian duct (in both male and females), Sertoli cells, Leydig cells, and granulosa cells. Expression of AMHRII persists in the adult female reproductive tract and has also been detected in the nervous system [13,14,15].

In addition to its role in normal reproductive physiology, AMH is now recognized as an important clinical marker for diagnosing and assessing reproductive disorders in both men and women. In males, serum AMH can be used to assess Sertoli cell function in children with intersex states that can help to distinguish between defects of male sexual differentiation caused by abnormal testicular determination and those resulting from isolated impairment of testosterone secretion or action [16]. In females, the serum AMH level is a reliable marker for the size of the ovarian follicle pool and a predictor of the ovarian response to controlled ovarian hyperstimulation [17]. Furthermore, AMH levels are 2-3 fold higher in women with polycystic ovary syndrome (PCOS) and there is a correlation between the severity of the disease and AMH levels [18]. It has been suggested that the increased follicular growth, which occurs during the early stages of PCOS, may be due to a deficiency of AMH [19], while the follicular arrest observed at later stages could be due to excessive AMH levels [20].

AMH and AMHRII have also been of interest in the field of oncology. AMHRII is expressed on a number of tumors and tumor cell lines [3,21], and AMH has been shown to inhibit the growth of some of these tumors [3]. In addition to developing AMH as a potential therapeutic [3], it has been suggested that agonist antibodies could be generated that bind specifically to AMHRII and trigger the regression of ovarian tumors, by mimicking the ability of AMH to assemble an active receptor signaling complex [22]. Alternatively, antibodies to AMHRII could be coupled to toxins to treat cancers that express AMHRII [23,24].

Various ELISA assays have been developed for detecting AMH and measuring AMH levels in human body fluids [25-27]. Most if not all of these assays employ monoclonal antibodies (mAbs) that detect the pro-region and mature domains. One of the mAbs is used to capture the AMH, while the other is biotinylated and used to detect the captured AMH. While these assays are very sensitive and can detect AMH at low levels in human body fluids, they do not distinguish between uncleaved inactive AMH and the cleaved active noncovalent AMH complex. To date, therefore, all AMH measurements made in normal and disease samples have reported total AMH levels (i.e. uncleaved AMH plus bioactive cleaved AMH) and have provided no information concerning the level of AMH that is active.

SUMMARY OF THE INVENTION

The present invention relates to soluble monomeric Anti-Mullerian Hormone Receptor type II (AMHRII) fusion proteins and uses thereof, in particular for detection or quantification of the bioactive cleaved form of Anti-Müllerian Hormone in a sample. In particular, the present invention is defined by the claims.

DETAILED DESCRIPTION OF THE INVENTION

Various ELISAs have been developed for measuring anti-Mullerian hormone (AMH) levels in human body fluids, but they do not distinguish between inactive uncleaved AMH and bioactive cleaved AMH, which can bind to the AMH type II receptor, AMHRII. Since it is possible that certain disease states may correlate with the level of active AMH, the inventors have developed an ELISA that detects bioactive cleaved AMH, through the use of a novel soluble AMHRII receptor. They have surprisingly found that when the dimeric soluble receptor AMHRII-Fc and endogenous AMHRII are synthesized in cells, both the secreted AMHRII-Fc and a portion of cellular AMHRII contain an interchain disulfide bond(s) that links single molecules into higher order oligomers via their extracellular domains. Furthermore, they have surprisingly found that when they produce a soluble AMHRII receptor, AMHRII-Fc/Fc, which only contains one extracellular domain and therefore no interchain disulfide bond, it has a higher affinity and stoichiometry for AMH than the dimeric AMHRII-Fc protein. This indicates that the disulfide bond compromises the ability of the dimeric AMHRII-Fc protein and probably endogenous AMHRII in cells to bind AMH. Because the AMHRII-Fc/Fc protein has a higher affinity for AMH, they have been able to use it to develop a sensitive ELISA for detecting bioactive cleaved AMH in human serum. These results poses the principle that a "soluble monomeric AMHRII fusion protein" (i.e. a protein which contains only one AMHRII extracellular domain) can be used to detect the bioactive cleaved form of Anti-Müllerian Hormone (i.e. bioactive cleaved AMH) in a sample, e.g. obtained from a subject (including humans but also other mammal species).

Accordingly, a first aspect of the present invention relates to a soluble monomeric AMHRII fusion protein wherein one AMHRII extracellular domain is fused to a heterologous polypeptide.

According to the invention, the soluble monomeric AMHRII fusion protein has the following characteristics: the protein is soluble in particular in biological fluids, the protein has the ability to bind bioactive cleaved AMH, and the protein contains only one AMHRII extracellular domain per molecule of fusion protein. Preferentially the soluble monomeric AMHRII fusion protein is produced in a eukaryotic cell.

As used herein the "AMHRII" has its general meaning in the art and refers to Anti-Mullerian Hormone Receptor type II (AMHRII). The term "AMHRII" includes naturally occurring AMHRII and function conservative variants thereof. The AMHRII can be from any source, but typically is a mammalian (e.g., human and non-human primate such as a cat, dog, cow, goat, sheep . . . ) AMHRII, and more particularly a human AMHRII. The sequence of AMHRII protein and nucleic acids for encoding such proteins are well known to those of skill in the art. For example, UniProtKB Acc. No Q16671 (SEQ ID NO:1) provides the complete amino acid sequence of Homo sapiens AMHRII. However, it should be understood that, as those of skill in the art are aware of the sequence of these molecules, any AMHRII protein or gene sequence variant may be used as long as it has the properties of a AMHRII.

"Function conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, most preferably at least 80%, and even more preferably at least 90%, and which has the same or substantially similar properties or functions as the native or parent protein to which it is compared.

As used herein the term "AMHRII extracellular domain" or "AMHRII ECD" has its general meaning in the art and refers to the domain of AMRHII which binds the active form of AMH. In particular, the extracellular domain of AMHRII comprises the amino acid sequence ranging from the residue at position 18 to the residue at position 145 in SEQ ID NO:1 or a function conservative variant thereof. Typically, the function conservative variant comprises an amino acid sequence having at least 80% of identity with the amino acid sequence ranging from the residue at position 18 to the residue at position 145 in SEQ ID NO:1. More particularly the function conservative variant comprises an amino acid sequence having 80, 81, 82, 83, 84, 85, 86, 87, 88, 89, 90, 91, 92, 93, 94, 95, 96, 97, 98, 99% of identity with the amino acid sequence ranging from the residue at position 18 to the residue at position 145 in SEQ ID NO:1. The capacity of a variant to bind bioactive cleaved AMH may be assessed by any conventional techniques known in the art. Examples of said conventional techniques are precipitation experiments and ELISA experiments as described here after in the experimental procedures.

In some embodiments, the soluble monomeric AMHRII fusion protein comprises one AMHRII extracellular domain that is fused either directly or via a spacer at its C-terminal end to the N-terminal end of the heterologous polypeptide, or at its N-terminal end to the C-terminal end of the heterologous polypeptide. As used herein, the term "directly" means that the (first or last) amino acid at the terminal end (N or C-terminal end) of the polypeptide is fused to the (first or last) amino acid at the terminal end (N or C-terminal end) of the heterologous polypeptide. In other words, in this embodiment, the last amino acid of the C-terminal end of said polypeptide is directly linked by a covalent bond to the first amino acid of the N-terminal end of said heterologous polypeptide, or the first amino acid of the N-terminal end of said polypeptide is directly linked by a covalent bond to the last amino acid of the C-terminal end of said heterologous polypeptide. As used herein, the term "spacer" refers to a sequence of at least one amino acid that links the polypeptide of the invention to the heterologous polypeptide. Such a spacer may be useful to prevent steric hindrances.

As used herein, the tem "heterologous polypeptide" refers to any polypeptide which is not a part of AMHRII and which consists of a "tag" that can be used to detect and/or immobilize the soluble monomeric AMHRII fusion protein of the invention. "Tag" means any polypeptide that facilitates its association with another molecule.

In some embodiments, the heterologous polypeptide comprises domains for the recognition sequence for enzymes; for associating non-proteinaceous molecules such as biotin or carbohydrates or any other post-translational modification of the protein. As a non-limiting example, the following polypeptide sequences can be a tag selected from the group consisting of a biotin accepting peptide sequence (e.g. biotin carboxyl carrier peptide), hexa-His peptide, Strep-Tag, Strep-Tagil, FLAG, c-myc, human influenza hemagglutinin (HA), maltose binding protein (MBP), glutathione-S-transferase (GST), green fluorescent protein (GFP), red fluorescent protein (RFP), blue fluorescent protein (BFP), chitin binding protein, calmodulin binding protein (CBP), cellulose binding domain, S-tag, FIAsH, RsaA, and other similar types of peptide sequences having the ability to facilitate association with another molecule. For instance biotin accepting peptide sequences are described in U.S. Pat. No. 5,723,584 issued on Mar. 3, 1998, U.S. Pat. No. 5,874,239 issued on Feb. 23, 1999, U.S. Pat. No. 5,932,433, issued on Aug. 3, 1999 and U.S. Pat. No. 6,265,552, issued July 2001.

In some embodiments, the heterologous polypeptide is chosen in a manner that an antibody can be raised against it.

In some embodiments, the heterologous polypeptide is an Fc domain.

As used herein the term "Fc domain" has its general meaning in the art and is used to define a C-terminal region of an immunoglobulin heavy chain, including native sequence Fc domains and variant Fc domains. Typically, the Fc domain of IgG consists of the CH2 and CH3 constant region domains. Although the boundaries of the Fc domain of other immunoglobulin heavy chains might vary, the human IgG-1 heavy chain Fc domain is usually defined to stretch from an amino acid residue at position 111 to the carboxyl-terminus thereof. In some embodiments, the Fc domain is obtained from any immunoglobulin, such as IgG-1, IgG-2, IgG-3, or IgG-4 subtypes, IgA (including IgA-1 and IgA-2), IgE, IgD or IgM. In a particular embodiment, the Fc domain is a native sequence Fc domain. In a particular embodiment, the Fc domain is a variant Fc domain. In still another embodiment, the Fc domain is a functional Fc domain. In some embodiments, the Fc domain comprises an amino acid sequence ranging from the residue at position 104 to the residue at position 330 in SEQ ID NO:2 (UniProtKB Accession P01857). Residues 104 to 110 encode for part of the hinge region, which connects the Fab and Fc regions and contains two cysteines that form inter-chain disulfide bonds between two IgG heavy chains.

The AMHRII extracellular domain can be fused to the N-terminus or C-terminus of the Fc domain. In some embodiments, the C-terminal end of the AMHRII extracellular domain is fused to the N-terminal end of the Fc domain.

In some embodiments, the soluble monomeric AMHRII fusion protein of the present invention consists of a first chain having an AMHRII extracellular domain fused to a Fc domain and a second chain consisting of a Fc domain wherein the chains are disulfide bonded within their Fc domains.

The soluble monomeric AMHRII fusion protein of the present invention of the invention is prepared according to any method well known in the art. Typically, the soluble monomeric AMHRII fusion protein is recombinantly prepared by transforming a host cell with a vector which comprises a nucleic acid molecule encoding for the protein.

In some embodiments, when the soluble monomeric AMHRII fusion protein of the present invention consists of a first chain having an AMHRII extracellular domain fused to a Fc domain and a second chain consisting of a Fc domain wherein the chains are disulfide bonded within their Fc domains, it can be prepared according to the method described in the EXAMPLE. Briefly, a host cell is transformed with a vector comprising a nucleic acid molecule encoding for the first chain (i.e. the first chain having an AMHRII extracellular domain fused to a Fc domain) and with a vector encoding comprising a nucleic acid molecule encoding for the second chain (i.e. the chain having a single Fc domain). 3 proteins are expected to be expressed by the host cell: a dimeric AMHRII-Fc protein, the soluble monomeric AMHRII fusion protein of the present invention and a dimeric Fc protein. The soluble monomeric AMHRII fusion protein of the present invention may be then purified and isolated according to any well known method in the art. Typically a ratio of 1 vector encoding the first chain for 1 vector encoding the second chain is preferably used for the preparation of the soluble monomeric AMHRII fusion protein of the present invention.

Typically the nucleic acid molecule is a cDNA molecule.

As used herein, the terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

In some embodiments, the vector is a bicistronic vector that includes the two nucleic acid molecules (i.e. the nucleic acid molecule encoding for the first chain and the nucleic acid molecule encoding for the second chain).

Any expression vector for animal cell can be used. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like. Other examples of plasmids include replicating plasmids comprising an origin of replication, or integrative plasmids, such as for instance pUC, pcDNA, pBR, and the like. Other examples of viral vectors include adenoviral, retroviral, herpes virus and AAV vectors. Such recombinant viruses may be produced by techniques known in the art, such as by transfecting packaging cells or by transient transfection with helper plasmids or viruses.

Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478. Examples of promoters and enhancers used in the expression vector for animal cell include early promoter and enhancer of SV40, LTR promoter and enhancer of Moloney mouse leukemia virus, promoter and enhancer of immunoglobulin H chain and the like.

The term "transformation" means the introduction of a "foreign" (i.e. extrinsic or extracellular) nucleic acid molecule to a host cell, so that the host cell will express the introduced nucleic acid molecule to produce the desired substance, typically a protein or enzyme coded by the introduced gene or sequence. A host cell that receives and expresses introduced DNA or RNA has been "transformed".

In some embodiments, the host cell is a eukaryotic cell. Typical eukaryotic cell lines such as CHO, BHK-21, COS-7, C127, PER.C6, YB2/0 or HEK293 could be used, for their ability to process to the right post-translational modifications of the soluble monomeric AMHRII fusion protein of the present invention. 293 c18 cells (also called 293E cells; ATCC number CRL-10852) express the Epstein Barr virus (EBV) nuclear antigen 1 (EBNA1) protein and are particularly useful for expressing genes on vectors that also contain the EBV origin of replication (oriP).

Accordingly, a further aspect of the invention relates to a host cell transformed with a nucleic acid molecule encoding for the first chain and with a nucleic acid molecule encoding for the second chain. The soluble monomeric AMHRII fusion protein of the present invention is then obtained by the host cell of the invention and recovering the soluble monomeric AMHRII fusion protein of the present invention expressed by the host cell, from the culture. The soluble AMHRII fusion protein of the present invention is then purified by conventional procedures, known in themselves to those skilled in the art, for example by fractional precipitation, in particular ammonium sulfate precipitation, electrophoresis, gel filtration, affinity chromatography, etc. . . .

The soluble monomeric AMHRII fusion protein of the present invention may find various applications.

In some embodiments, the soluble monomeric AMHRII fusion protein of the invention is used for detection and quantification of the bioactive cleaved form of Anti-Müllerian hormone (AMH) (i.e. bioactive cleaved AMH) in a sample.

As used herein, the term "Anti-Müllerian Hormone" (AMH) corresponds to a 140 kDa glycoprotein hormone. AMH is synthesized as a large precursor with a short signal sequence followed by the pre-pro hormone that forms homodimers. Prior to secretion, the mature hormone undergoes glycosylation and dimerisation to produce a 140-kDa dimer of identical disulphide-linked 70-kDa monomer subunits; each monomer contains an N-terminal domain (also called the "pro" region) and a C-terminal domain (also called the "mature" region). "Uncleaved AMH" as used herein corresponds to the 140-kDa dimer of identical disulphide-linked 70-kDa monomer subunits; each monomer contains an N-terminal domain (also called the "pro" region) and a C-terminal domain (also called the "mature" region). Approximately 10% of AMH produced in cells and secreted into the medium is cleaved at monobasic sites to generate 110-kDa N-terminal and 25-kDa C-terminal homodimers which remain associated in a non-covalent complex. Thus "secreted AMH", as used herein contains about 90% 140 kDa homodimer and about 10% cleaved non-covalent complex. "Bioactive cleaved AMH" as used herein corresponds to the 110-kDa N-terminal and 25-kDa C-terminal homodimers which remain associated in a non-covalent complex, as defined in Pepinsky et al., 1988. "N-terminal AMH" as used herein corresponds to the 110-kDa N-terminal homodimer, as defined in Pepinsky et al., 1988. "C-terminal AMH" as used herein corresponds to the 25-kDa C-terminal homodimer, as defined in Pepinsky et al., 1988. As shown in Pepinsky et al. 1988, uncleaved AMH can be converted to completely bioactive cleaved AMH by treatment with the protease plasmin.

Accordingly a further aspect of the present invention relates to a method for detecting or quantifying the presence of bioactive cleaved AMH in a sample, said method comprising contacting the sample with a soluble monomeric AMHRII fusion protein of the invention.

In some embodiments, the sample is a biological sample, such as tissue extracts, cell lysates or culture medium, or is a body fluid such as whole blood, serum, plasma, follicular fluid, seminal fluid, synovial fluid, cerebrospinal fluid, saliva, or urine. In a particular embodiment, the sample is a serum sample, a whole blood sample, a plasma sample, a follicular fluid sample, a seminal fluid sample.

Typically the detection or quantification of bioactive cleaved AMH is achieved by any methods known in the art using a soluble monomeric AMHRII fusion protein of the invention. Examples of said methods include, but are not limited to, standard electrophoretic and immunodiagnostic techniques such as western blots, radioimmunoassay, ELISA (enzyme-linked immunosorbant assay), "sandwich" immunoassay, immunoradiometric assay, gel diffusion precipitation reaction, immunodiffusion assay, precipitation reaction, agglutination assay (such as gel agglutination assay, hemagglutination assay, etc.), complement fixation assay, immuno fluorescence assay, protein A assay, immunoelectrophoresis assay, high performance liquid chromatography, size exclusion chromatography, solid-phase affinity, etc.

In some embodiments, the soluble monomeric AMHRII fusion protein of the present invention comprises a label such as a chemiluminescent agent, a colorimetric agent, an energy transfer agent, an enzyme, a fluorescent agent, or a radioisotope. Examples of chemiluminescent agent include an enzyme that produces a chemiluminescent signal in the presence of a substrate(s) that produce chemiluminescent energy when reacted with the enzyme. Examples of such an enzyme include horseradish peroxidase (HRP) and alkaline phosphatise (AP). Other examples of a chemiluminescent agent include a non-enzymatic direct chemiluminescent label, such as Acrinidium ester system. Examples of a colorimetric agent include an enzyme such as horseradish peroxidase, alkaline phosphatase, and acetylcholine esterase (AChE). Examples of energy transfer agent include fluorescent lanthanide chelates. Examples of fluorescent agents include fluorescent dyes. Examples of radioisotopes include $^{125}I$, $^{14}C$ and $^{3}H$. The label may be coupled directly or indirectly by any known method in the art.

In some embodiments, the detection or quantification of bioactive cleaved AMH in a sample is achieved with a solid support wherein the soluble monomeric AMHRII fusion protein of the present invention is immobilized on it (e.g. coated directly or indirectly on it). The solid support may be in the form of plates, test-tubes, beads, microparticles, filter paper, membrane, glass filters, magnetic particles, glass or silicon chips or other materials known in the art.

In some embodiments, the soluble monomeric AMHRII fusion protein of the present invention is immobilized on the support when an antibody coated on the surface of the solid support binds to the heterologous polypeptide.

In some embodiments, the soluble monomeric AMHRII fusion protein of the present invention is directly immobilized on the support by the heterologous polypeptide (e.g. a Fc domain) that is coated on the surface of the solid support.

In some embodiments, the method for detecting or quantifying the presence of bioactive cleaved AMH of the present invention comprises the step of contacting the sample with a soluble monomeric AMHRII fusion protein which consists of a first chain having an AMHRII extracellular domain fused to a Fc domain and a second chain consisting of a Fc domain wherein the chains are disulfide bonded within their Fc domains.

In said embodiment, the immunoassay according to the invention may involve the use of said soluble monomeric AMHRII fusion protein of the invention in combination with an anti-AMH antibody. Typically, the anti-AMH antibody is used as to "detect" the AMH and the soluble monomeric AMHRII fusion protein is used to "capture" the AMH. Examples of said assay are ELISA experiments as described here after in the EXAMPLE. In some embodiments, the detection and quantification of bioactive cleaved AMH in a sample are achieved by i) providing a solid support coating with an amount of antibodies specific for the Fc domain of the soluble monomeric AMHRII fusion protein of the invention (e.g. goat anti-Fc antibodies as described in the EXAMPLE), ii) adding an amount of the soluble monomeric AMHRII fusion protein of the invention, iii) bringing the sample containing AMH into contact with the solid support, iv) adding an amount of the anti-AMH antibody which is conjugated to a first label and v) adding an amount of a binding partner which is specific for the label of the AMH-antibody and which is conjugated to second label. While the soluble monomeric AMHRII fusion protein captures the AMH present in the sample, the anti-AMH antibody binds to the AMH (i.e. to create "sandwich" complexes) and the binding partner conjugated with the second label binds the first label conjugated to the anti-AMH antibody. Measuring the amount of bound binding partner which is specific for the label of the anti-AMH antibody reveals the amount of AMH present in the sample. Typically, the anti-AMH antibody is directed to an epitope directed to the C-terminal region of AMH, which does not prevent the interaction between bioactive cleaved AMH and the extra-cellular domain of AMHRII of the fusion protein. An example of such antibody includes the mouse monoclonal mAb 22A2. Typically the first label is biotin and the binding partner is therefore streptavidin. In some embodiments, streptavidin is conjugated with HRP (horseradish peroxidise). Typically washing steps (with any appropriate buffer such as PBS with or without an non-ionic detergent) are performed after steps i), ii), iii), iv), and v). Typically, a blocking step is performed after step i) with a buffer containing BSA or milk and/or serum (goat or bovine) to block non-specific binding of the proteins added in steps ii) through v).

The methods for detection and quantification of bioactive cleaved AMH as described above are particularly suitable in diagnostic assays.

The diagnostic method of the invention may be carried out with any subject. The subject is preferably a mammal, in particular a human. However, the diagnostic methods of the invention also find applications in the veterinary field and may be applied to any mammal subject such as a cat, dog, cow, goat, sheep . . . The subjects may be male or female and may be of any age, including prenatal (i.e., in utero), neonatal, infant, juvenile, adolescent, adult, and geriatric subjects.

In particular, an object of the present invention relates to a diagnostic method for determining the fertility of a subject (i.e. a human or not), for predicting controlled ovarian hyperstimulation success rate, for diagnosing intersex disorders like androgen insensitivity and gonadal dysgenesis, for assessing male puberty (in particular for boys suffering from precocious puberty) or for diagnosing and/or monitoring the presence of a cancer in a subject in need thereof, said method comprising quantifying bioactive cleaved AMH in a sample obtained from said subject, as described here above.

In some embodiment, the diagnostic method is intended for diagnosing and/or monitoring the presence of a cancer in a subject. Typically, the cancer is an AMH type II receptor and/or AMH-expressing cancer. In some embodiments, the method is intended for diagnosing and/or monitoring a cancer, said cancer being a neoplasm stemming from granulosa cell tumours, an ovarian cancer, a breast cancer, a uterine cancer or a prostate cancer. In a particular embodiment, the cancer is an ovarian cancer which stems from granulosa cell tumours. In some embodiments, the cancer is a testicular cancer.

In some embodiment, the diagnostic method is intended for determining the fertility of a subject. In some embodiments, the diagnostic method of the invention is intended for determining the fertility of female subject. In some embodiments, the diagnostic method of the invention is intended for determining the fertility of a male subject.

In some embodiments, the diagnostic method is intended for predicting controlled ovarian hyperstimulation success rate. Controlled ovarian hyperstimulation is a technique used in assisted reproduction involving the use of fertility medications to induce ovulation by multiple ovarian follicles. Typically, controlled ovarian hyperstimulation consists in the administration of one active ingredient selected from the group consisting of GnRH agonists or antagonists associated with recombinant follicle-stimulating hormone (FSH) or human Chorionic Gonadotropin (hCGH).

In some embodiment, the diagnostic method is particularly suitable in diagnostic assays for intersex disorders like androgen insensitivity or in diagnostic assays for hypogonadotropic hypogonadism. The method is also particularly suitable for the assessing problems with male puberty, in particular for boys suffering from gonadal dysgenesis.

Another object of the invention is a method for diagnosing persistent müllerian duct syndrome (PMDS) in a subject in need thereof, said method comprising quantifying bioactive cleaved AMH in a sample obtained from said subject, as described here above. Typically the method is for diagnosing PMDS that are caused by mutation(s) in AMH gene.

According to the invention, the diagnostic method for determining the fertility of a subject or for diagnosing and/or monitoring the presence of a cancer or for diagnosing PMDS in a subject in need thereof, comprises the steps of i) providing a sample obtained from a subject, ii) contacting the sample with a soluble monomeric AMHRII fusion protein of the present invention as defined here above under conditions appropriate for formation of a complex between the soluble monomeric AMHRII fusion protein and the bioactive cleaved AMH present in the sample, iii) quantifying the amount of complexes formed to determine the amount of bioactive cleaved AMH present in the sample, and iv) correlating the amount of bioactive cleaved AMH with the determination of the fertility of a subject or with the diagnosis and/or the monitoring of a cancer or with the diagnosis of PMDS in a subject.

The amount of bioactive cleaved AMH quantified may thus be compared with a predetermined reference value that is for example the corresponding amount detected in the samples of control subjects, or in previous samples obtained from the subject. In some embodiments, the predetermined reference values refer to the amount of at least one of the biological forms of AMH that can be determined by the method of the invention in a subject that has not been diagnosed for a cancer or in a subject that is considered as being fertile or in a subject that has not been diagnosed for PMDS. Typically, a higher amount of total AMH in a sample than the predetermined reference value is indicative of a fertility of a subject, whereas a lower amount than the predetermined reference value is a marker of infertility. The ability to measure bioactive cleaved AMH by the method of the invention may allow these correlations and assessments to be more precise. A higher amount of total AMH in a sample compared to predetermined reference value is indicative of the presence of a cancer. Quantifying the amount of bioactive cleaved AMH is also of interest for monitoring for example the efficacy of surgery and cancer recurrence. Hence, serum AMH levels usually normalizes within few days following surgery, thus persistent AMH levels are indicative of residual cancer. Typically; a lower amount of total AMH in a sample compared to the predetermined reference value is indicative of the presence of PMDS. Again, the ability to measure bioactive cleaved AMH by the method of the invention may provide better monitoring and/or diagnoses in cancer and PMDS.

Another object of the invention is a kit for use in the method of the invention as described here above which comprises a soluble monomeric AMHRII fusion protein of the present invention.

In some embodiments, the kit comprises a soluble monomeric AMHRII fusion protein which consists of a first chain having an AMHRII extracellular domain fused to a Fc domain and a second chain consisting of a Fc domain wherein the chains are disulfide bonded within their Fc domains. In said embodiments, the kit of the present invention also comprises an anti-AMH antibody. Typically, the anti-AMH antibody is directed to an epitope directed to the C-terminal region of AMH, which does not prevent the interaction between bioactive cleaved AMH and the extra-cellular domain of AMHRII of the fusion protein. An example of such antibody includes the mouse monoclonal mAb 22A2. Typically, the anti-AMH antibody is labelled with biotin. In some embodiments, the kit of the present invention comprises i) a soluble monomeric AMHRII fusion protein of the present invention, ii) an anti-AMH antibody as above described labelled with biotin, iii) a solid support coated with anti-Fc domain antibodies (e.g. goat anti-Fc antibodies), and iv) a streptavidin binding partner conjugated with HRP.

The kit may also contain optional additional components for performing the method of the invention. Such optional components are for example containers, mixers, buffers, instructions for assay performance, labels, supports, and any additional reagents for performing the method. Another optional component is recombinant bioactive cleaved AMH to generate standard curves.

The soluble monomeric AMHRII fusion protein of the invention may also find therapeutic applications. In particular, the soluble monomeric AMHRII fusion protein may represent a decoy receptor that can trap the circulating bioactive cleaved AMH and thus acts as an AMH antagonist. In some embodiments, the soluble monomeric AMHRII fusion protein consists of a first chain having an AMHRII extracellular domain fused to a Fc domain and a second chain consisting of a Fc domain wherein the chains are disulfide bonded within their Fc domains.

In particular, the soluble monomeric AMHRII fusion protein of the present invention can be used for improving female fertility and/or for treating female infertility disorders and/or for improving or treating male infertility. As used herein, the term "improving female fertility" generally refers to increasing the chance of conception. For instance, the soluble monomeric AMHRII fusion protein of the present invention is suitable for improving controlled ovarian hyperstimulation success rate. Typically, the soluble monomeric AMHRII fusion protein of the present invention exerts its effect by increasing the recruitment of primordial follicles, but also by increasing FSH sensitivity of the follicles. Soluble monomeric AMHRII fusion protein of the present inventions may also find application in techniques of fertility-preservation in patients with cancer based on ovarian tissue cryopreservation.

Subjects that may receive a treatment for improving fertility may be females of any mammal species, including humans. In certain embodiments, the soluble monomeric AMHRII fusion protein of the present invention is administered to a woman and in particular to a woman during her reproductive years. In other embodiments, the soluble monomeric AMHRII fusion protein of the present invention is administered to female domesticated animal (e.g., cattle, sheep, goats, horses, and the like) or to a female companion animal (e.g., dog, cat, and the like).

Typically the soluble monomeric AMHRII fusion protein of the present invention is administered to the subject in an effective amount, i.e. an amount that is sufficient to fulfill its intended purpose. The exact amount of the soluble monomeric AMHRII fusion protein of the present invention to be administered will vary from subject to subject, depending on the age, sex, weight and general health condition of the subject to be treated, the desired biological or medical response (e.g., recruitment of primordial follicles, improvement of female fertility, and the like). In many embodiments, an effective amount is one that increases the recruitment of primordial follicles.

Typically the soluble monomeric AMHRII fusion protein of the present invention (optionally after formulation with one or more appropriate pharmaceutically acceptable carriers or excipients), in a desired dosage is administered to a subject in need thereof by any suitable route. Various delivery systems are known and can be used to administer the soluble monomeric AMHRII fusion protein of the present inventions including tablets, capsules, injectable solutions, encapsulation in liposomes, microparticles, microcapsules, etc. Methods of administration include intravenous administration of a liquid composition, transdermal administration of a liquid or solid formulation, oral, topical administration, or interstitial or inter-operative administration. Administration may be affected by the implantation of a device whose primary function may not be as a drug delivery vehicle. Administration may also be performed by incubation in an ex-vivo sample (ex. ovarian biopsy).

As mentioned above, the soluble monomeric AMHRII fusion protein of the present inventions is administered per se or as a pharmaceutical composition. Accordingly, the present invention provides pharmaceutical compositions comprising an effective amount of a soluble monomeric AMHRII fusion protein of the present invention and at least one pharmaceutically acceptable carrier or excipient.

The invention will be further illustrated by the following figures and examples. However, these examples and figures should not be interpreted in any way as limiting the scope of the present invention.

FIGURES

FIG. 1. Model showing processing of AMH, assembly of the AMH receptor signaling complex, and intracellular signaling.

Figure 2:
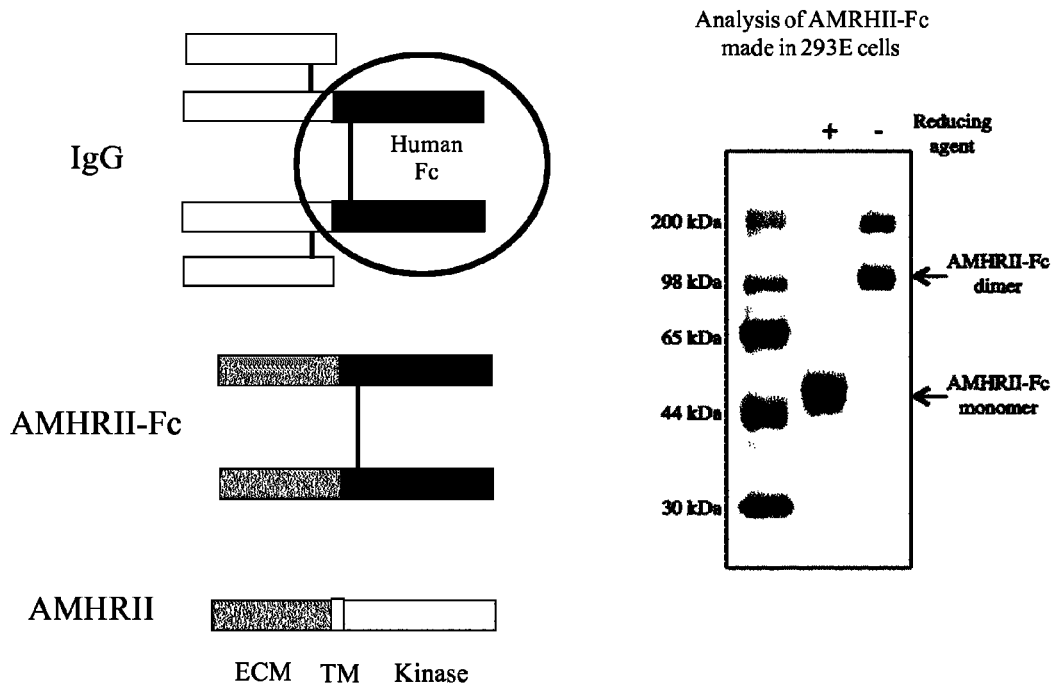

FIG. 2. Schematic diagram showing IgG, AMHRII and the AMHRII-Fc fusion protein. ECD: extracellular domain. TM: transmembrane domain. SDS-PAGE analysis of the AMHRII-Fc fusion protein analyzed under reducing and non-reducing conditions and detected by staining with Coomassie Blue.

Figure 3:
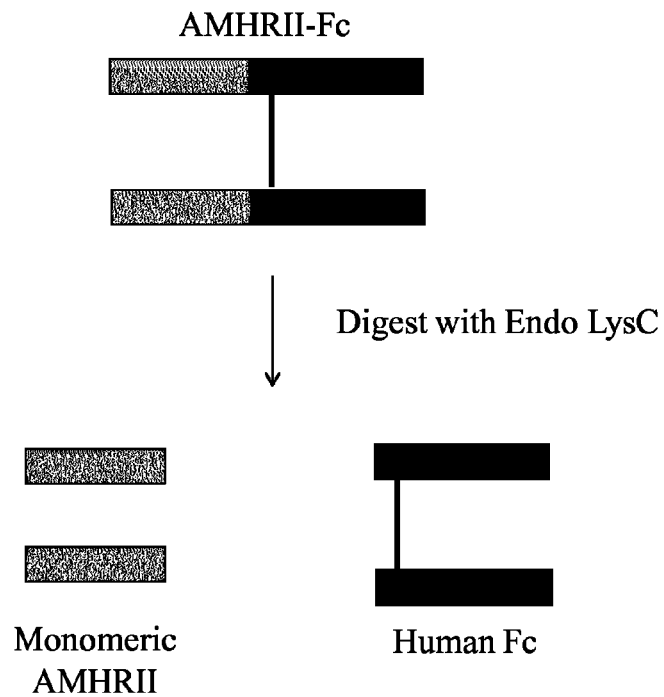

FIG. 3. Schematic diagram showing a strategy for generating a monomeric form of the AMHRII ECD. A cleavage site for endoproteinase LysC is located very close to the junction of the AMHRII ECD and the Fc domain. At this point, it was not known that the ECDs were connected covalently by a disulfide bond(s).

Figure 4:
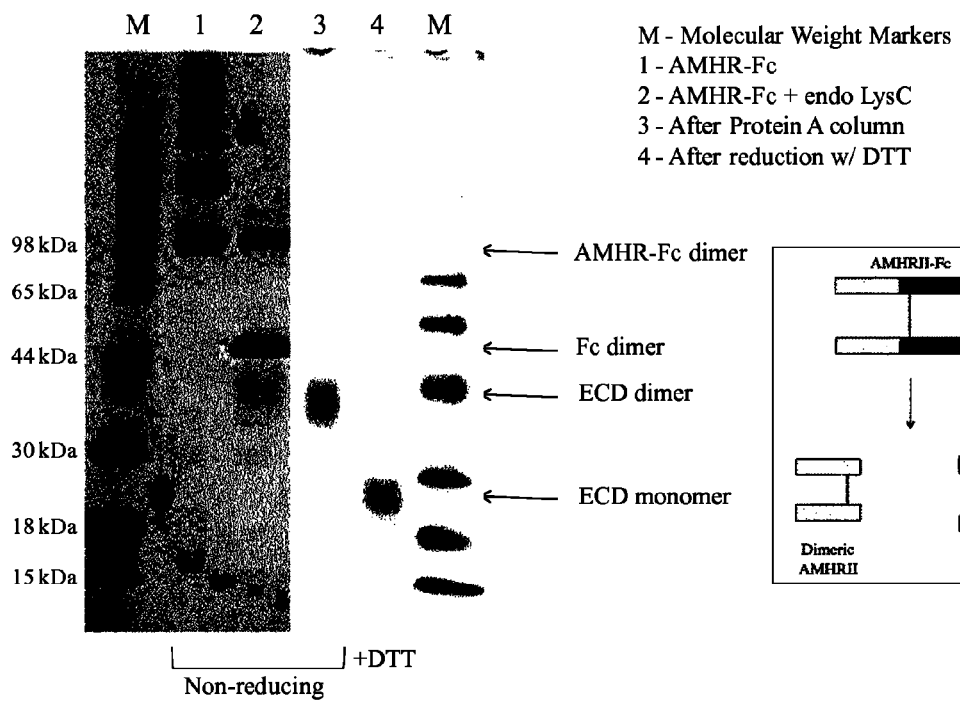

FIG. 4. SDS-PAGE analysis of AMHRII-Fc digested with endoproteinase LysC. After digestion with LysC, the Fc containing proteins were removed with Protein A Sepharose. The ECD ran as a dimer with a MW around 42 kDa before reduction, and as a monomer with a MW around 23 kDa after reduction, indicating that the ECDs were linked covalently by a disulfide bond, as shown in the schematic diagram.

Figure 5:
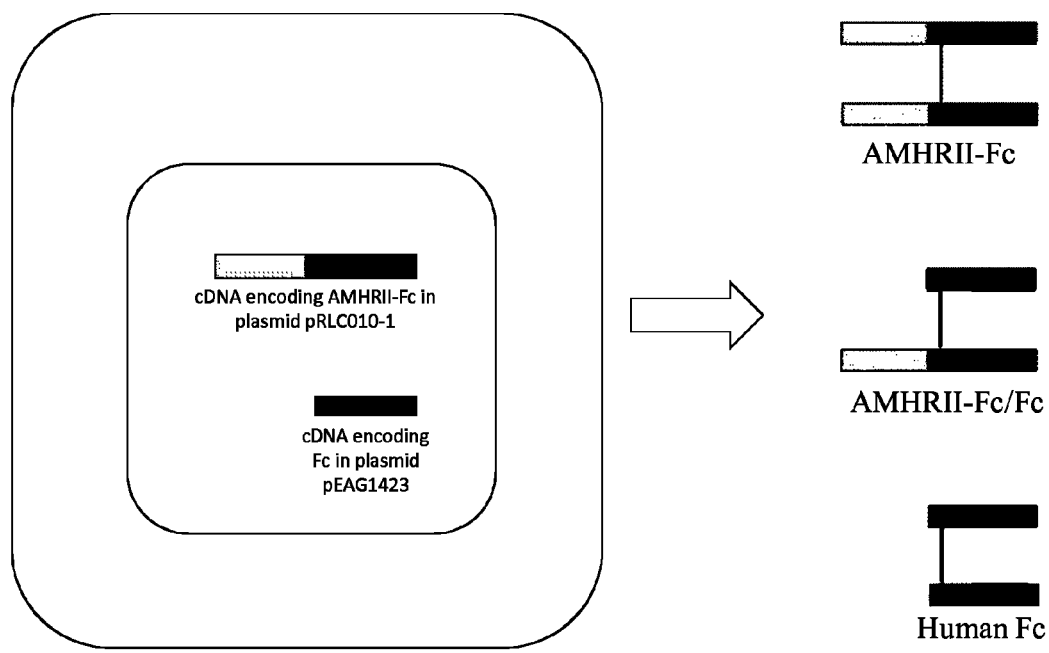

FIG. 5. Schematic diagram showing another strategy for generating a monomeric version of the AMHRII ECD. An expression vector (pRLC010-1) containing a cDNA encoding for the AMHRII-Fc fusion protein was co-expressed with another expression vector (pEAG1423) containing a cDNA encoding a signal sequence and the hinge, CH2, CH3 domains of human IgG1 in 293E cells. The three proteins expected to be produced by the transfected cells are shown.

Figure 6:
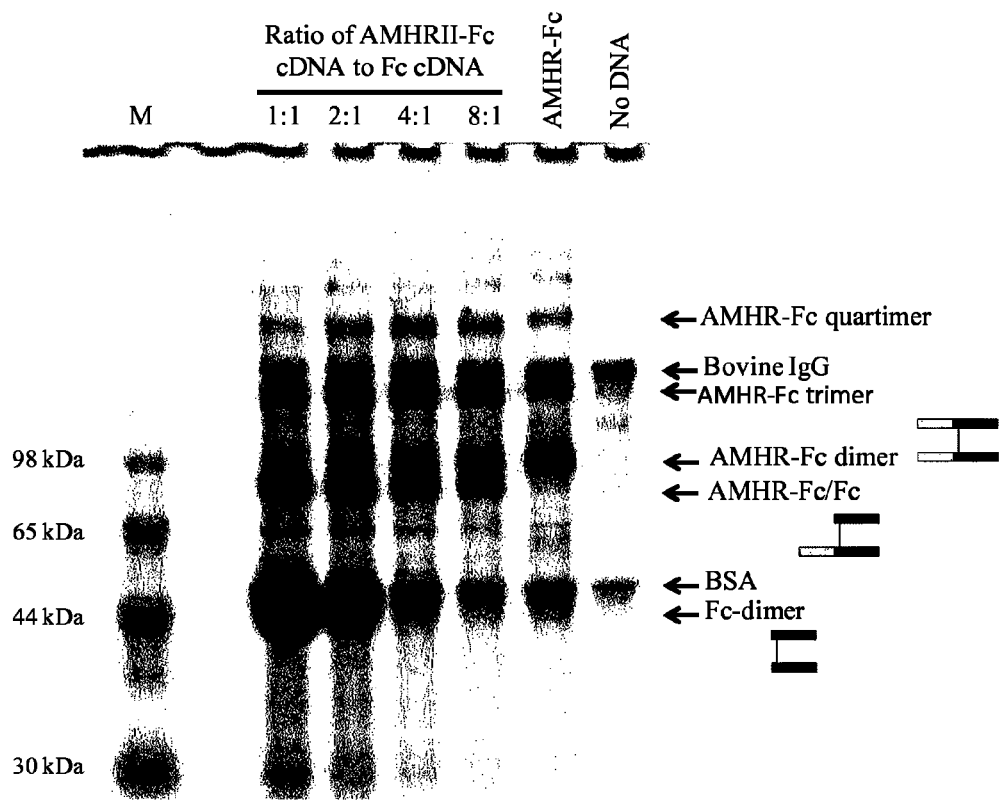

FIG. 6. SDS-PAGE analysis of 293E cells transfected with vectors containing AMHRII-Fc and Fc cDNAs at various ratios. The dimeric AMHRII-Fc fusion protein, the dimeric Fc protein, and the heterodimeric AMHRII-Fc/Fc protein were all detected.

Figure 7:
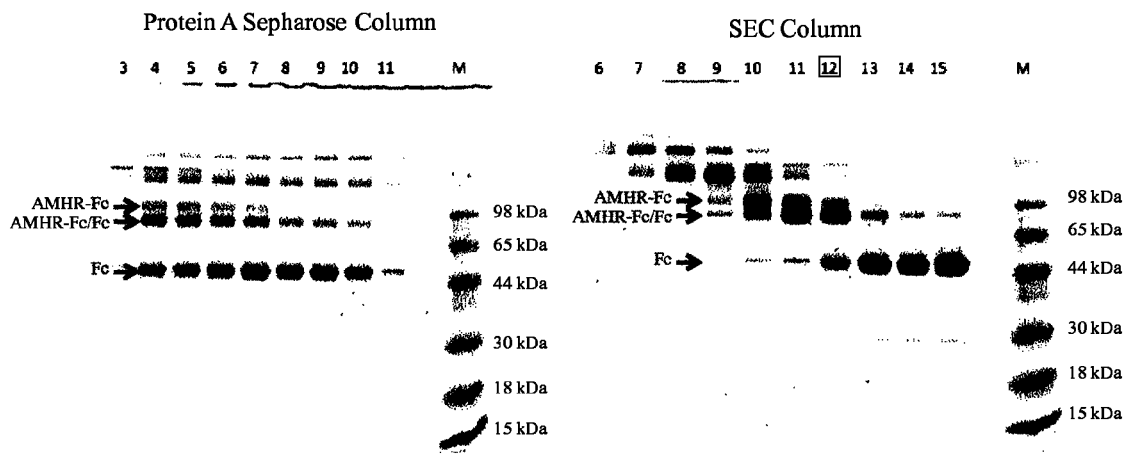

FIG. 7. SDS-PAGE analysis of fractions from the Protein A Sepharose and size exclusion chromatography columns used to purify the AMHRII-Fc/Fc fusion protein.

Figure 8:
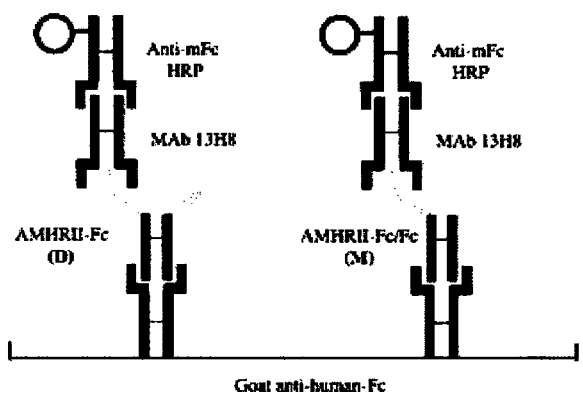
Figure 8:
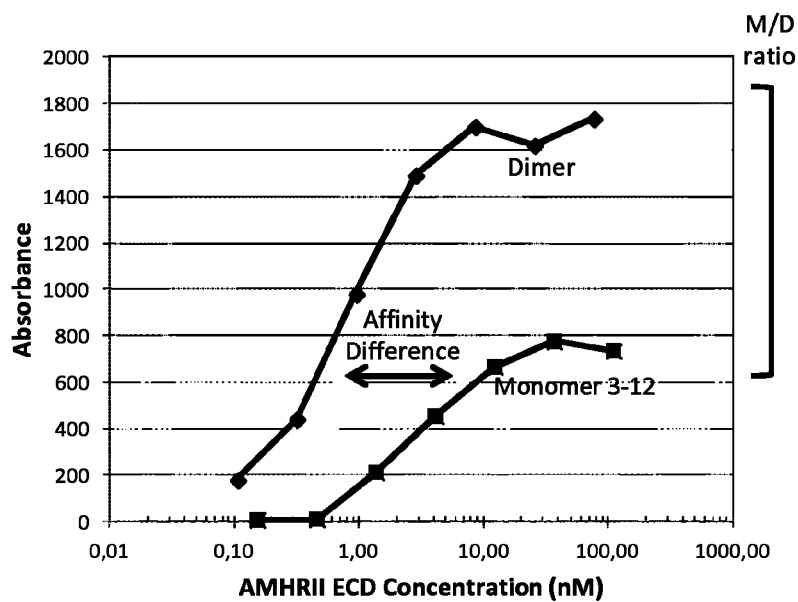

FIG. 8. AMHRII-Fc binds anti-AMHRII mAb 13H8 with a higher affinity and stoichiometry than AMHRII-Fc/Fc. The schematic shows the ELISA setup used to assess binding of mAb 13H8 to AMHRII-Fc and AMHRII-Fc/Fc. (The schematic is only intended to show the steps for the ELISA and should not be construed to imply monovalent or bivalent interactions.) Soluble receptors at various concentrations were captured by a goat anti-human Fc antibody coated on the ELISA plate, incubated with mAb 13H8, and bound 13H8 was detected with a goat anti-mouse Fc antibody conjugated to horseradish peroxidase (HRP).

Figure 9:
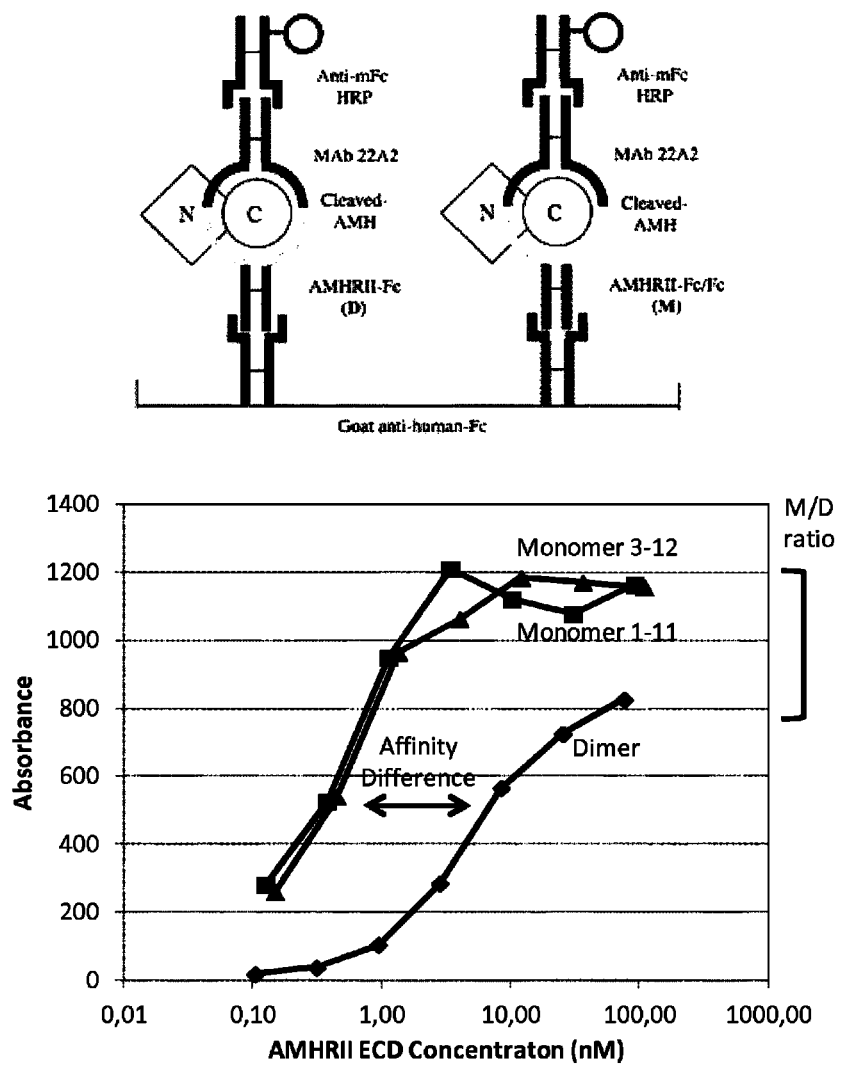

FIG. 9. AMHRII-Fc/Fc binds bioactive cleaved AMH with a higher affinity and stoichiometry than AMHRII-Fc. The schematic shows the ELISA setup used to assess binding of bioactive cleaved AMH to AMHRII-Fc and AMHRII-Fc/Fc. Soluble receptors at various concentrations were captured by a goat anti-human Fc antibody coated on the ELISA plate, incubated with bioactive cleaved AMH, and bound bioactive cleaved AMH was detected with an anti-C-terminal AMH mAb (22A2) and a goat anti-mouse Fc antibody conjugated to HRP. Two different preparations of AMHRII-Fc/Fc were analyzed.

Figure 10:
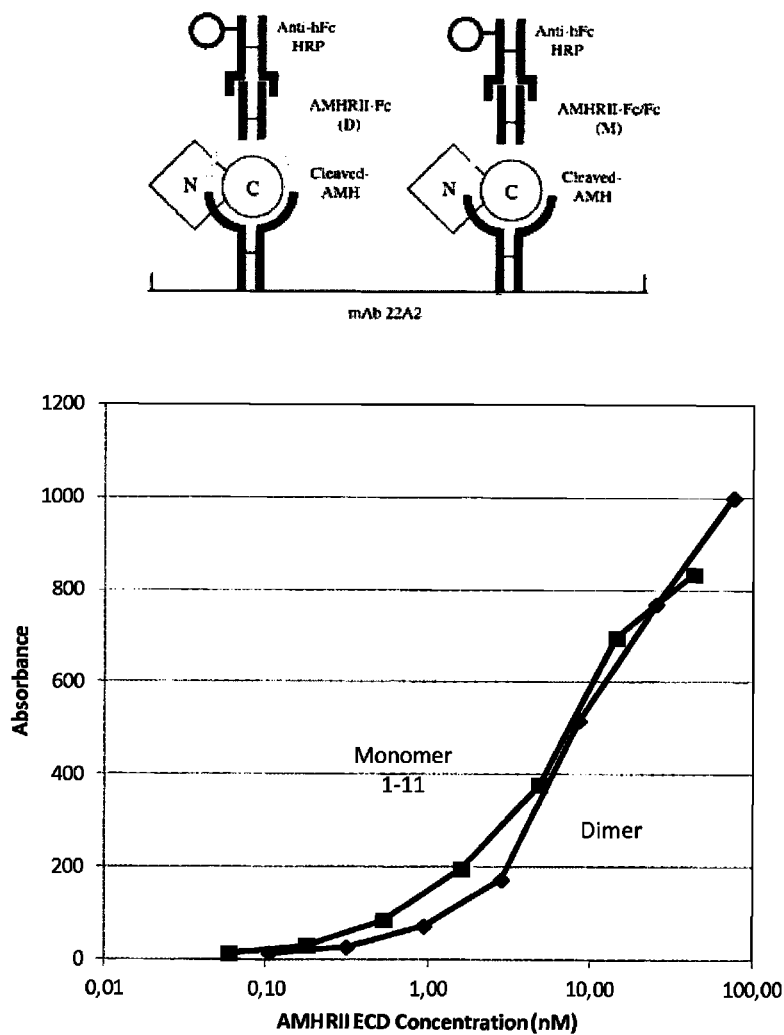

FIG. 10. AMHR-Fc (D) and AMHR-Fc (M) show similar binding behavior to cleaved-AMH when presented in solution. The schematic shows the ELISA setup used to assess binding of soluble receptors to bioactive cleaved AMH captured on anti-C-terminal AMH mAb 22A2.

FIG. 11. Development of a sensitive ELISA for active cleaved AMH using a new high affinity soluble type II receptor. A) The schematic diagram shows the ELISA formats used to detect cleaved AMH with the two soluble receptors. AMHRII-Fc or AMHRII-Fc/Fc (1 ug/ml) was captured on a goat anti-human Fc antibody coated on the ELISA plate, and incubated with cleaved AMH at various concentrations. Bound cleaved AMH was detected with a biotinylated anti-C-terminal mAb (22A2) and streptavidin conjugated to HRP. B) AMHRII-Fc/Fc showed a higher signal than AMHRII-Fc at all concentrations of cleaved AMH tested. The inset shows that the responses are linear in the 1 to 10 ng/ml range. Data points are averages of six replicates. C) Three different batches of AMHRII-Fc/Fc purified by size exclusion chromatography showed similar responses in the ELISA. The inset shows SDS-PAGE analysis of the three batches under non-reducing conditions after staining with Coomassie Blue. Data points are averages of six replicates. D) Cleaved AMH diluted in human serum could be detected with high sensitivity with the ELISA employing the AMHRII-Fc/Fc receptor. Cleaved AMH was diluted into either assay buffer (PBS containing 1% BSA and 1% goat serum) or human serum (containing no detectable cleaved or uncleaved AMH) at 100 ng/ml, and diluted down the plate two fold with assay buffer. The sensitivity of the assay was still in the 1 to 10 ng/ml range; the inset shows that the response was linear in this range. As a negative control, AMHRII-Fc (3 ug/ml) treated with sodium metaperiodate and no longer capable of binding cleaved AMH, was substituted for AMHRII-Fc/Fc. Data points are averages of two replicates.

FIG. 12. The cAMH-ELISA does not detect uncleaved AMH. A) The schematic diagram shows the ELISA format for detecting both cleaved and uncleaved (total) AMH. AMH was captured on an anti-N-terminal AMH mAb (10.6) and detected with a biotinylated anti-C-terminal mAb (22A2) and streptavidin conjugated to HRP. B) The ELISA for total AMH detected cleaved and uncleaved AMH with similar sensitivity. C) The schematic diagram showing the cAMH-ELISA format is explained in the legend to FIG. 2A. D) Only cleaved AMH was detected with the cAMH-ELISA; the inset shows that the response to cleaved AMH was linear in the 1 to 10 ng/ml range. For both ELISAs, uncleaved and cleaved AMH were diluted into human serum at 100 ng/ml, and diluted down the plate two fold with assay buffer. Data points are averages of two replicates.

FIG. 13. Measurement of cleaved AMH levels and the level of AMH cleavage in samples containing a mixture of cleaved and uncleaved AMH. Six samples were prepared containing varying levels of uncleaved and cleaved AMH in 90% human serum and total AMH was measured using the ELISA for total AMH (FIG. 3A) or cleaved AMH was measured using the cAMH-ELISA (FIG. 3B). The actual levels of total and cleaved AMH in each sample were recalculated using the experimentally determined values for total AMH in the Control 0 (0% cleaved) and Control 100 (100% cleaved) samples, which contained only uncleaved or cleaved AMH, respectively. A) Experimental versus actual values for total AMH in the six samples. B) Experimental versus actual values for cleaved AMH in the six samples. C) Experimental versus actual values for the level of AMH cleavage in the six samples. The level of AMH cleavage (experimental and actual) in each sample was calculated by dividing the cleaved AMH level by the total AMH level in that sample (experimental and actual). Experimental values shown in A are the averages of six data points; experimental values shown in B are the averages of N data points indicated above the bar.

Figure 14:
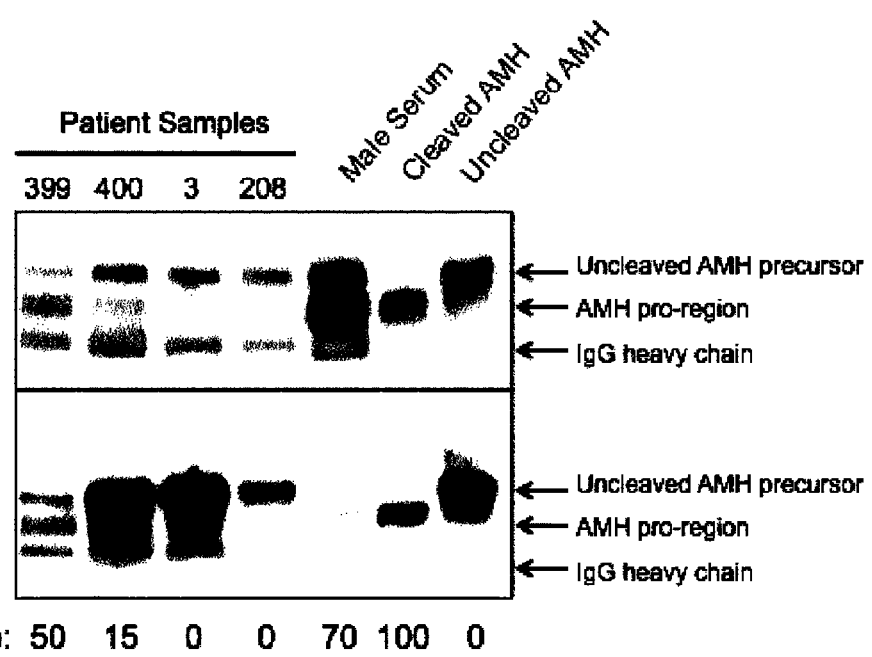

FIG. 14. Characterization of AMH in patient samples by biochemical analysis. AMH in patient follicular fluid was captured with an anti-N-terminal AMH mAb (10.6) conjugated to Sepharose, analyzed by SDS-PAGE under reducing conditions, followed by western blotting using an anti-AMH polyclonal Ab (L44). Uncleaved and cleaved AMH were run as controls to allow identification of the uncleaved AMH precursor and the N-terminal pro-region produced after cleavage. The band that runs just below the pro-region band is the human IgG heavy chain, which is detected by the secondary anti-rabbit Fc Ab. The level of AMH cleavage in the patient samples was estimated from the intensities of the uncleaved AMH precursor and N-terminal pro-region bands.

EXAMPLE

Methods:

Digestion of AMHRII-Fc with Endoproteinase LysC. AMHRII-Fc, shown in FIG. 2, was prepared as previously described [8]. To separate the ECD and Fc domains, 487 µg of AMHRII-Fc was incubated with 0.65 µg of endoproteinase LysC in a volume of 1 ml for 60 min at 37 C and 30 min at room temperature. 20 µl of 2 mM leupeptin was added to stop the digestion, followed by 200 µl of Protein A Sepharose (50% suspension in PBS), and the tube was rocked for 45 min at room temperature. After centrifugation to remove the Fc domain bound to the resin, the supernatant was collected and the recovered AMHRII ECD protein was estimated at 120 µg, as determined by SDS-PAGE. To reduce the AMHRII ECD protein, 60 µg of AMHRII ECD protein was incubated with 0.1 mM TCEP in a volume of 606 µl for 60 min at 37 C. NEM was added to 1 mM to quench the reaction and Tris (pH 7.4) was added to 10 mM. The proteins were stored at −80 C.

Production and purification of AMHRII-Fc/Fc. A soluble monomeric AMHRII fusion protein was generated, AMHRII-Fc/Fc, which contains one AMHRII-Fc chain and one Fc chain that are disulfide bonded within the Fc domains (FIG. 5). An expression vector (pRLC010-1) containing a cDNA encoding for the AMHRII-Fc fusion protein was co-expressed with another expression vector (pEAG1423) containing a cDNA encoding a signal sequence and the hinge, CH2, CH3 domains of human IgG1 in 293E cells. Both vectors contain the EBV origin of replication (oriP), which allows them to replicate episomally in 293E cells, due to expression of the EBNA1 protein.

In a pilot experiment, different ratios of the two vectors were used to assess the optimal conditions for producing the AMHRII-Fc/Fc protein. 293E cells (plated in 6 well plates 24 hours earlier; 9.6 cm$^2$ culture area/well) were transfected with a total of 2 µg DNA of the two plasmids at various ratios as shown in FIG. 6 or only the pRLC010-1 plasmid expressing the AMHRII-Fc fusion protein. The transfections were performed using lipofectamine 2000 (Invitrogen) and the manufacturer's recommended conditions. The cells were placed in a $CO_2$ incubator for 2 days at 37 C. Conditioned medium (1.5 ml) was collected from the wells, 40 µl of Protein A Sepharose (50% suspension in PBS) was added, and the tubes were rocked for 40 minutes at room temperature. The resin was washed three times with phosphate buffered saline (PBS) and the protein was eluted from the resin by addition of 30 µl 2× non-reducing sample buffer and heating at 65 C for 10 min. Eluted proteins were subjected to SDS-PAGE (4-20% gradient gel) under non-reducing conditions, and detected by staining with Coomassie blue.

In the large scale transfection, 293E cells were plated into 4 triple flasks (500 cm$^2$ culture area/triple flask; 100 ml medium/triple flask) and transfected with a total of 400 µg of plasmids pRLC010-1 and pEAG1423 (at a 1:1 ratio) using lipofectamine 2000 as described above. Conditioned medium was collected every 2 days over the next 12 days. To recover the Fc containing proteins, 2 liters of conditioned medium were loaded on a 2 ml Protein A Sepharose column overnight by gravity. The column was washed with PBS (6×1.5 ml), followed by 25 mM NaPhosphate (pH 5.5), 100 mM NaCl (6×1.5 ml). The Fc containing proteins were eluted with 25 mM NaPhosphate (pH 2.8), 100 mM NaCl. 0.5 ml fractions were collected and neutralized by adding 25 µl of 0.5 M NaPhosphate (pH 8.6). The fractions were analyzed by obtaining absorption spectra from 240 to 320 nm and by SDS-PAGE. Individual fractions from the Protein A Sepharose column were further resolved by size-exclusion chromatography (SEC), using a Fast Protein Liquid Chromatography (FPLC) system and a Superdex 200 column. 0.25 ml of fraction #6 from the Protein A Sepharose column, containing 2.55 mg protein, was loaded on the column, eluted with PBS at the rate of 20 ml/hr, and 0.5 ml fractions were collected. The fractions were analyzed as above. All fractions were stored at −80 C.

ELISAs. AMH proteins and anti-AMH mAbs were previously described [8,25]. The ELISA for detecting total AMH (cleaved and uncleaved) in human serum employed an anti-pro-region mAb coated on the plate (either mAb 10.6 or 11F8) to capture the AMH, and a biotinylated anti-C-terminal AMH mAb (mAb 22A2) to detect the captured AMH. This assay is similar to those that have been published previously [25-27]. The ELISA for measuring soluble AMHRII receptor binding to bioactive cleaved AMH captured on an anti-C-terminal AMH mAb (22A2; coated on an ELISA plate), has been previously described [8].

To compare the properties of the dimeric AMHRII-Fc and monomeric AMHRII-Fc/Fc fusion proteins for binding bioactive cleaved AMH, ELISA plates (Nunc Maxisorp) were coated with a goat anti-human Fc antibody (Jackson ImmunoResearch; catalog #109-005-098) overnight at 4° C. in 50 mM sodium bicarbonate, pH 9.6 (10 µg/ml; 50 µl/well). The plates were washed five times with water and then blocked for 1-2 h at room temperature using 150 µl/well of block buffer containing 1% BSA (Sigma; A-7906) and 1% goat serum (Invitrogen; 16210064) in PBS. This buffer was used for all subsequent dilutions. The block buffer was discarded and the receptor fusion proteins were serially diluted down the plate by a factor of three. Plates were incubated for 1 h, followed by five washes with PBS. 50 µl of bioactive cleaved AMH was added to each well at a concentration of 1 µg/ml and incubated for 2 h. The plates were washed five times with PBS/0.05% Tween-20. Mouse anti-C-terminal AMH mAb 22A2 was added at a concentration of 1 µg/ml and the plates were incubated for 1 h. After five washes with PBS/0.05% Tween-20, goat anti-mouse Fc conjugated to HRP (Jackson ImmunoResearch) was added at a 1:3000 dilution and the plates were incubated for 1 h. After five washes with PBS/0.05% Tween-20, 50 µl of TMB substrate were added to each well. The reactions were quenched by the addition of 50 µl/well of 2M sulfuric acid and absorbances were read at 450 nm.

To compare the properties of the dimeric AMHRII-Fc and monomeric AMHRII-Fc/Fc fusion proteins for binding mouse anti-AMHRII mAb 13H8, the conditions were as described above except for the following changes. After the incubation with the receptor fusion proteins and the subsequent washes with PBS, mAb 13H8 was added at a concentration of 1 µg/ml, and the plates were incubated for 1 hour. After five washes with PBS/0.05% Tween-20, goat anti-mouse Fc conjugated to HRP (Jackson ImmunoResearch) was added and the plates were developed as described above.

To measure the level of bioactive cleaved AMH, either diluted into human serum or in patient serum, the conditions were as described above for bioactive cleaved AMH detection except for the following changes. After the blocking step, AMHRII-Fc/Fc protein was added to the wells at a concentration of 3 µg/ml (34 nM) and incubated for 1 h. After five washes with PBS, bioactive cleaved AMH (diluted into BSA buffer or human serum) or patient samples were serially diluted down the plate by a factor of two, and the plates were incubated for 2 h. After five washes with PBS/0.05% Tween-20, biotinylated mouse anti-C-terminal AMH mAb 22A2 was added at a concentration of 1 µg/ml and the plates were incubated for 1 h. After five washes with PBS/0.05% Tween-20, strepavidin conjugated to HRP (Jackson ImmunoResearch) was added at a 1:3000 dilution and the plates were incubated for 1 h and developed as described above. As a negative control, AMHRII-Fc, which had been treated with sodium meta-periodate, was used in place of AMHRII-Fc/Fc at a concentration of 3 µg/ml. The periodate treated AMHRII-Fc is almost completely inactive in binding bioactive cleaved AMH.

Results:

AMHRII-Fc contains an interchain disulfide bond(s) between AMHRII ECD monomers. In order to get an accurate measurement of the affinity of AMHRII for bioactive cleaved AMH, we wanted to make a monomeric form of AMHRII. As shown in FIG. 2, the AMHRII-Fc fusion protein that we made several years ago is dimeric, due to interchain disulfide bonds between two Fc domains. Thus each fusion protein molecule contains two extracellular domains (ECD)s. The gel analysis in FIG. 2 confirms that AMHRII-Fc consists mostly of dimer and a smaller amount of tetramer and higher order oligomers. The presence of two ECD domains can make a measurement of the affinity of AMHRII-Fc for AMH difficult, because there can be an increase in the apparent affinity for AMH due to an avidity effect, which is the accumulated strength of the individual binding interactions.

To generate a monomeric version of the AMHRII ECD, we digested AMHRII-Fc with endoproteinase LysC, which cleaves after lysines and has been used to remove the Fc fragment from antibodies (FIG. 3). As shown in lane 2 of FIG. 4, digestion with LysC resulted in the generation of two lower molecular weight (MW) bands: the Fc fragment running at around 54 kDa and a more diffuse band running just below the 44 kDa protein marker. After incubation of the digested proteins with Protein A Sepharose to remove Fc containing proteins, the most prominent band left in the supernatant was the diffuse band running around 40-42 kDa. This band was presumed to be the AMHRII ECD, but because the MW of the AMHRII ECD monomer should be around 13.6 kDa, we suspected that the ECD might be migrating on the gel as a dimer. This was confirmed after reduction of the 40-42 kDa band with DTT yielded a band of approximately 22 kDa (FIG. 4; lane 4). This indicates that there is at least one interchain disulfide bond between ECD monomers within the AMHRII-Fc fusion protein, as shown in the insert in FIG. 4.

We have now confirmed that a fraction of endogenous AMHRII expressed in the mouse SMAT1 cell line and human AMHRII transfected into COS cells form higher MW oligomers. These higher MW oligomers are converted to a 72 kDa species (the MW of monomeric AMHRII) on SDS-PAGE after reduction, consistent with the higher oligomers containing at least one interchain disulfide bond between AMHRII ECDs. It is unlikely that the disulfide bond could be between intracellular domains, since the disulfide bond would be unstable due to the reducing environment of the cell. The discovery that AMHRII exists as a disulfide linked dimer in cells was an unexpected result, since AMHRII is thought to be dimerized by interaction with AMH, and that AMHRII would most likely exist on the surface of cells as a monomer (see FIG. 1). We wanted to assess whether the interchain disulfide bond(s) could affect the ability of AMHRII to bind AMH. However, we found that neither the purified ECD dimer nor monomer, generated after LysC cleavage, could bind AMH. We suspected that this was a result of the LysC digestion; there is only one lysine in the ECD of AMHRII, but it is in a loop near the N-terminus and would be very exposed to the LysC proteinase. Thus, in order to assess the effect of the interchain disulfide bond(s) on AMH binding, we had to find an alternative way to generate a monomeric form of the AMHRII ECD.

Production of AMHRII-Fc/Fc, a soluble monomeric AMHRII receptor. A soluble AMHRII fusion protein, which is monomeric (i.e contains only one ECD monomer per molecule), was generated using the strategy shown in FIG. 5. An expression vector (pRLC010-1) containing a cDNA encoding for the AMHRII-Fc fusion protein was co-expressed with another expression vector (pEAG1423) containing a cDNA encoding a signal sequence and the hinge, CH2, CH3 domains of human IgG1 (i.e. most of the Fc domain) in 293E cells. Three proteins are expected to be produced by the 293E cells: dimeric AMHRII-Fc, dimeric Fc, and a disulfide linked dimer composed of one chain of AMHRII-Fc and one chain of Fc, which we refer to as AMHRII-Fc/Fc. The later protein is monomeric (with respect to AMHRII) since it only contains one AMHRII ECD.

We first performed a pilot experiment to verify that the 293E cells were producing all three proteins and to determine the optimal ratio of the two plasmids for transfection. As shown in FIG. 6, all three proteins were detected in the conditioned medium of 293 cells co-transfected with the two plasmids. At a 1:1 ratio of the two plasmids, a higher amount of Fc dimer was produced, but also a lower amount of AMHRII-Fc dimer was produced. At higher ratios of the AMHR-Fc and Fc cDNAs, less Fc dimer was produced, but higher amounts of AMHRII-Fc dimer were produced. Since it was considered critical to separate as much AMHRII-Fc dimer from the AMHRII-Fc/Fc protein during subsequent purification steps, a ratio of 1:1 was chosen in order to minimize production of the AMHRII-Fc dimer.

A large scale preparation of AMHRII-Fc/Fc was performed. 293E cells in 4 triple flasks were transfected at an AMHRII-Fc cDNA to Fc cDNA ratio of 1:1 and conditioned medium was collected every two days over the next 12 days. The AMHRII-Fc/Fc protein was purified as described in the METHODS section using Protein A Sepharose and size exclusion chromatography. SDS-PAGE analysis (under non-reducing conditions) of fractions collected after both chromatography steps is shown in FIG. 7. Fraction 12 from the SEC column was used for experiments described below (referred to as 3-12). Another fraction collected from a different SEC column, referred to as 1-11, was also analyzed.

Monomeric AMHRII-Fc/Fc has a higher affinity for cleaved active AMH than dimeric AMHRII-Fc. We first compared AMHRII-Fc/Fc to AMHRII-Fc in terms of their ability to bind a mouse anti-AMHRII mAb (13H8). The ELISA format is shown in FIG. 8. A goat anti-human Fc antibody was coated on the ELISA plate and the two soluble receptors were captured at various concentrations. Assay wells containing captured soluble receptors were then incubated with mAb 13H8, and bound mAb 13H8 was detected with an anti-mouse Fc secondary antibody. As shown in FIG. 8, AMHRII-Fc bound a higher level of mAb 13H8 and with a higher affinity than AMHRII-Fc/Fc. Since AMHRII-Fc has two AMHRII ECDs, while AMHRII-Fc/Fc has only one, it would be expected that AMHRII-Fc should bind twice as much of mAb 13H8 as AMHRII-Fc/Fc. In fact, in the ELISA shown on FIG. 8, AMHRII-Fc/Fc bound a little less than half the amount bound by AMHRII-Fc. This is almost certainly due to the contamination of the AMHRII-Fc/Fc preparation by Fc; thus the M/D ratio can be used to correct for contaminating Fc.

The difference in affinity for mAb 13H8 exhibited by the two receptors may also be due to the fact that AMHRII-Fc has two ECDs. Even at low concentration, mAb 13H8 can bind to AMHRII-Fc bivalently because of the two ECDs, and therefore bind AMHRII-Fc with a higher apparent affinity due to the avidity effect. In contrast, mAb 13H8 can only bind AMHRII-Fc/Fc bivalently at higher concentrations, when two AMHRII-Fc/Fc molecules are close enough together on the ELISA plate to allow binding by one 13H8 antibody.

Next we compared AMHRII-Fc/Fc to AMHRII-Fc in terms of their ability to bind bioactive cleaved AMH, using the ELISA format shown in FIG. 9. Surprisingly, the results were the exact opposite of those observed with mAb 13H8: AMHRII-Fc/Fc bound a higher level of bioactive cleaved AMH and with a higher affinity than AMHRII-Fc. The level of bioactive cleaved AMH bound at high concentrations of two receptors provides an indication of the number of functional ECDs in each receptor preparation (i.e. those capable of binding cleaved-AMH). For example, if the AMHRII-Fc preparation contained two functional ECDs, then it should be able to bind twice as much bioactive cleaved AMH as the AMHRII-Fc/Fc preparation, which only has one ECD. But, as shown in FIG. 9, the AMHRII-Fc preparation bound less cleaved-AMH than the AMHRII-Fc/Fc preparation, indicating that, on average, only one out of two (or less) of ECDs are functional in the AMHRII-Fc preparation. This may be due to the interchain disulfide bond(s) formed between two ECDs monomers of each AMHRII-Fc dimer, which renders some ECDs inactive for binding AMH.

AMHRII-Fc/Fc also bound bioactive cleaved AMH with a higher apparent affinity than AMHRII-Fc (approximately 10-20 fold higher). This may indicate that the AMHRII-Fc/Fc protein is more capable of making a bivalent interaction with bioactive cleaved AMH than the AMHRII-Fc protein, which should allow it to bind with a higher apparent affinity. The lower affinity of AMHRII-Fc for bioactive cleaved AMH may also be due to the interchain disulfide bond(s) formed between two ECD monomers of one AMHRII-Fc dimer. It is possible that the interchain disulfide bond(s) compromises the ability of AMHRII-Fc to bind bioactive cleaved AMH bivalently, as easily as AMHRII-Fc/Fc receptors.

To test our hypothesis that the higher affinity of AMHRII-Fc/Fc compared to AMHRII-Fc is due to its ability to more easily form a bivalent interaction with bioactive cleaved AMH, we assessed the ability of both soluble receptors to bind bioactive cleaved AMH captured on an ELISA plate. In this format, the soluble receptors are presented in solution, in a state where a monomeric receptor cannot bind bioactive cleaved AMH bivalently. As shown in FIG. 10, both soluble receptors behaved similar in this format in their ability to bind AMH, in terms of affinity and stoichiometry. This result allows a number of conclusions. 1) Dimeric AMHRII-Fc is functionally monomeric, since it binds bioactive cleaved AMH with a similar affinity as monomeric AMHRII-Fc/Fc. This is consistent with the results of FIG. 9, which indicate that AMHRII-Fc binds less bioactive cleaved AMH than AMHRII-Fc/Fc and that at least one ECD of each AMHRII-Fc dimer is non-functional. 2) The affinity of AMHRII-Fc/Fc for bioactive cleaved AMH is lower when the soluble receptor is presented in solution and cannot bind bioactive cleaved AMH bivalently, indicating that the higher affinity of AMHRII-Fc/Fc for bioactive cleaved AMH observed in FIG. 9 is due to its ability to bind bioactive cleaved AMH bivalently and therefore with a higher apparent affinity when presented on a surface. 3) Conversely, the lower affinity of AMHRII-Fc for bioactive cleaved AMH compared to AMHRII-Fc/Fc (FIG. 9) implies that it cannot form a bivalent interaction with bioactive cleaved AMH as easily as AMHRII-Fc/Fc when presented on a surface. The interchain disulfide bond(s) is the most likely explanation for this observation.

Overall, these results show that the AMHRII-Fc protein is compromised in its ability to bind bioactive cleaved AMH, presumably due to the disulfide bond(s) formed between ECDs. Since AMHRII also forms disulfide-bonded oligomers in cells, a portion of the endogenous AMHRII receptor in cells may also be compromised for binding bioactive cleaved AMH. This is a very unexpected finding. Furthermore we have also shown we can express a soluble version of the AMHRII ECD, which does not have this interchain disulfide bond, and binds bioactive cleaved AMH with a higher apparent affinity.

Figure 11A:
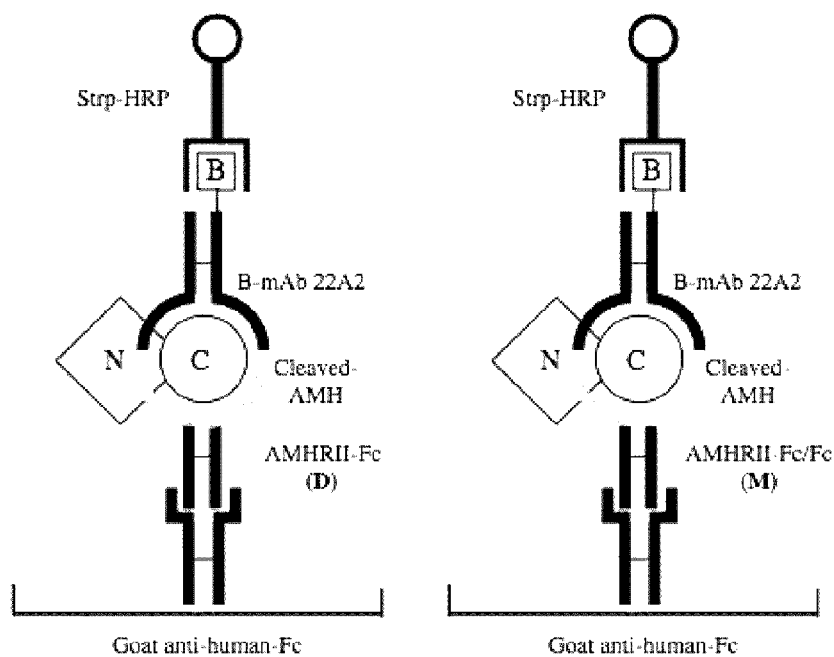
Figure 11B:
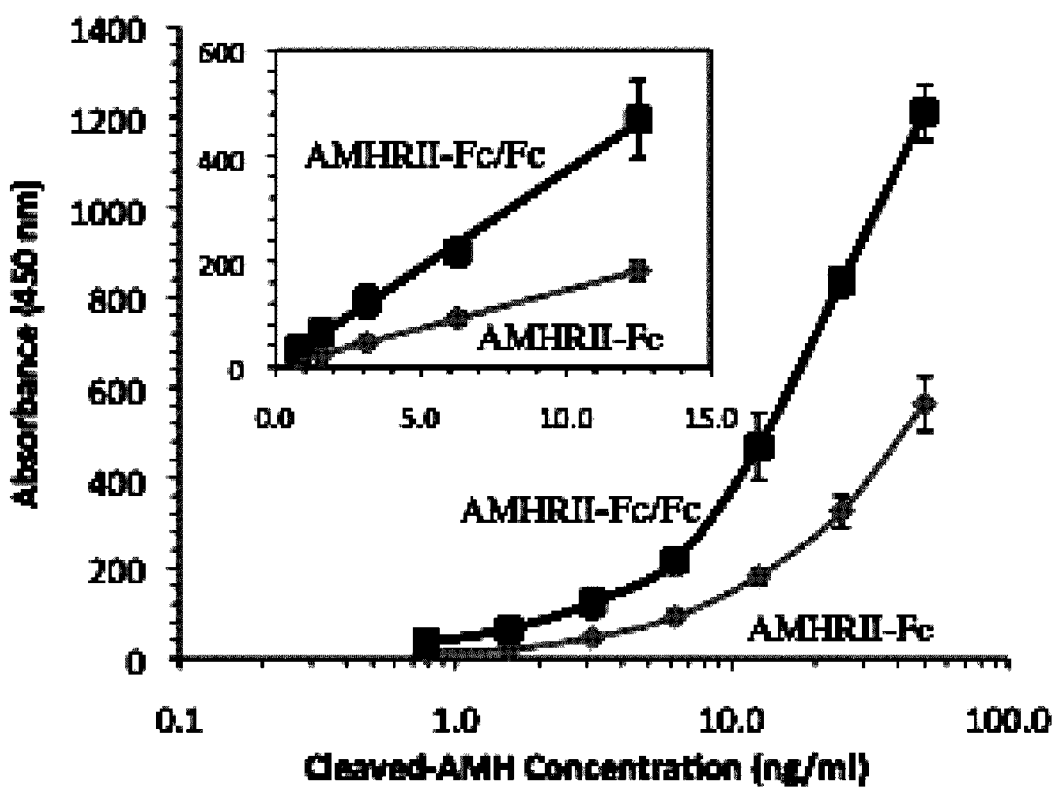
Figure 11C:
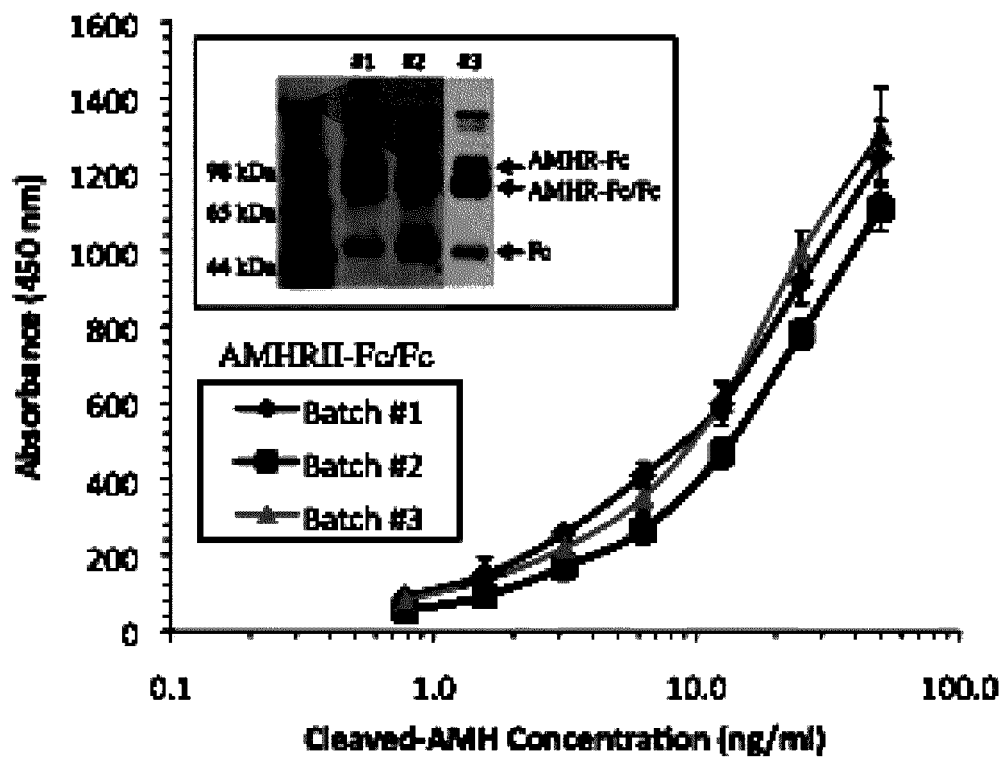

Development of a sensitive ELISA for active cleaved AMH. In order to develop an ELISA for active cleaved AMH, we tested a number of different formats using the AMHRII-Fc fusion protein. One ELISA format that was tested consisted of capturing cleaved AMH on anti-AMH mAbs coated on ELISA plates, followed by binding and detection of AMHRII-Fc. However, the sensitivity in this format was never better than 10 ng/ml (data not shown). In contrast, capture of the AMHRII-Fc fusion protein on an anti-human Fc Ab, followed by binding and detection of cleaved AMH, yielded better sensitivity, allowing detection below 10 ng/ml (FIG. 11B). Although this level of sensitivity was adequate for detecting cleaved AMH in assay buffer, it was not sufficient for reproducibly detecting AMH in human serum (data not shown). Because the AMHRII-Fc/Fc protein has a higher affinity and stoichiometry for binding cleaved AMH than AMHRII-Fc, we used it to improve the sensitivity of the ELISA for cleaved AMH, shown in the schematic diagram in FIG. 11A. The two fusion proteins were added at a constant concentration (1 µg/ml) to plates coated with an anti-human Fc Ab. After washing the plate, cleaved AMH was added at the indicated concentrations, and AMH bound to the soluble receptors was detected with biotinylated anti-C-terminal AMH mAb 22A2 and a streptavidin-HRP conjugate. As shown in FIG. 11B, AMHRII-Fc/Fc produced a higher signal than AMHRII-Fc at all concentrations of cleaved AMH tested and the response was linear in the 1 to 10 ng/ml ranges (inset). In FIG. 11C, three different preparations of AMHRII-Fc were tested and all gave consistent results. The lower signals observed with Batch #2 could be due to the higher level of contaminating Fc protein compared to the other two batches (FIG. 11C; inset).

Figure 11D:
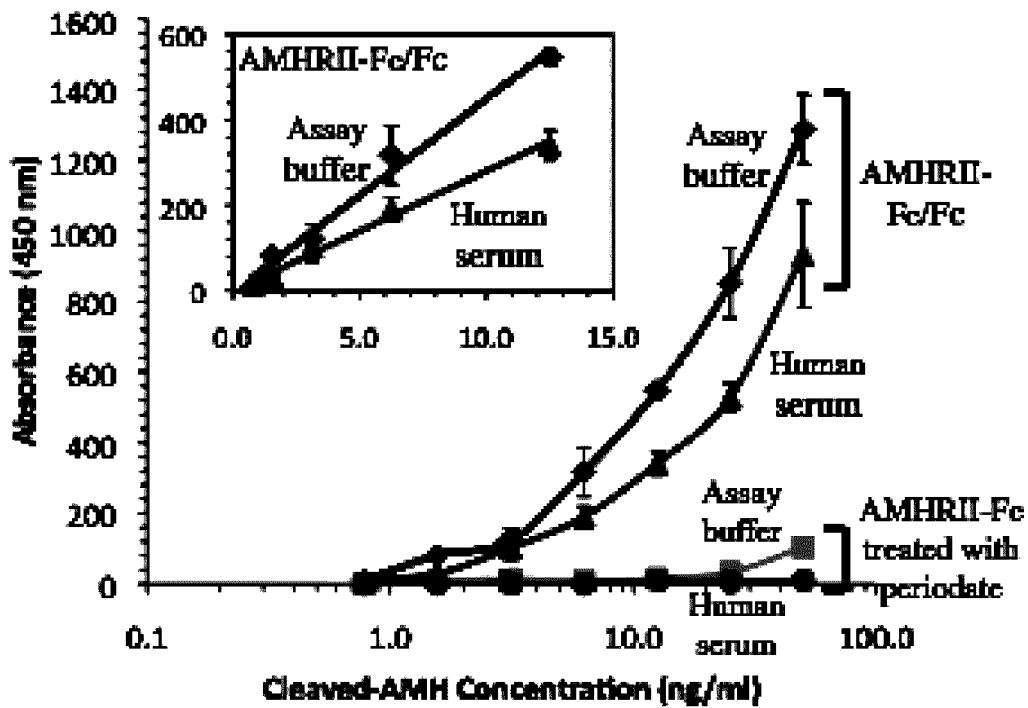

As shown in FIG. 11D, this ELISA format employing the AMHRII-Fc/Fc fusion protein could also detect cleaved AMH that had been diluted into human serum, in the same concentration range. The human serum used in this experiment and subsequent experiments was from an individual with a virtually undetectable level of AMH (measured with the ELISA that detects both cleaved and uncleaved AMH). There was a slight decrease in the signal when AMH was diluted into human serum, but the effect did not cause a problem with reproducibility. A negative control was also performed: AMHRII-Fc treated with sodium meta-periodate, which we have shown almost completely inactivates the receptor for binding AMH. When this fusion protein was used instead of AMHRII-Fc/Fc (FIG. 11D), little or no binding of cleaved AMH was observed, indicating that the signal observed with AMHRII-Fc/Fc results from specific binding to the cleaved AMH. We refer to this ELISA as the cAMH-ELISA, to distinguish it from the ELISAs that measure total AMH (cleaved and uncleaved).

The cAMH-ELISA can be used to measure the level of AMH cleavage in a sample containing a mixture of uncleaved and cleaved AMH. We wanted to test whether the cAMH-ELISA could be used to measure the level of cleaved AMH in a sample containing a mixture of uncleaved and cleaved AMH. But first it was necessary to demonstrate that the cAMH-ELISA only detects cleaved AMH and not uncleaved AMH, over a range of AMH concentrations. To do this, we compared the cAMH-ELISA to the conventional ELISA, which detects both forms of AMH. The total AMH ELISA (FIG. 12A) that we used is similar to those that are currently used for measuring AMH levels in patient samples: a biotinylated anti-C-terminal AMH mAb (22A2) is used to detect AMH captured on an anti-N-terminal AMH mAb (10.6). For uncleaved AMH, we used AMH produced in cells transfected with an AMH cDNA, which contains a mutation at the monobasic cleavage site; AMH produced by these transfected cells shows no evidence of cleavage by SDS-PAGE and is therefore completely uncleaved. As shown in FIG. 12B, the ELISA for total AMH detected cleaved and uncleaved AMH with similar sensitivity. In contrast, only cleaved AMH was detected by the cAMH-ELISA (FIG. 12C, D). In these ELISAs, both cleaved and uncleaved AMH had been diluted into human serum, showing that serum or components in the serum, do not affect the ability of AMHRII-Fc/Fc to specifically interact with cleaved AMH or cause it to non-specifically bind to uncleaved AMH.

Figure 13A:
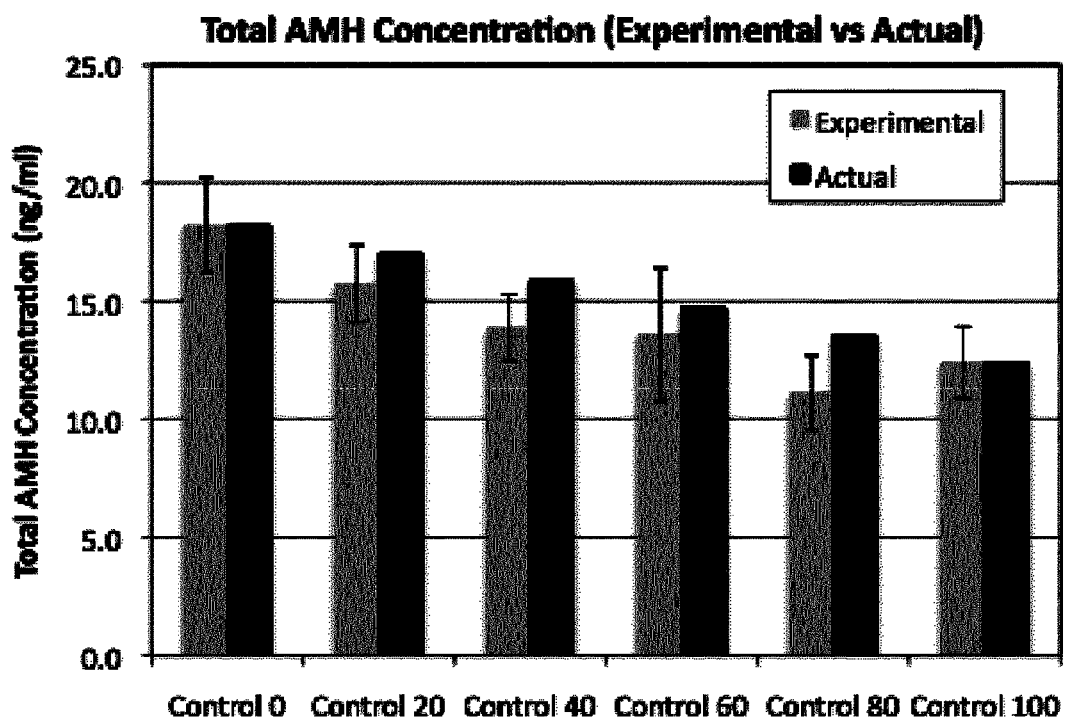

To test whether the cAMH-ELISA could accurately measure the level of cleaved AMH in samples containing a mixture of cleaved and uncleaved AMH, we prepared a series of samples containing various levels of cleaved AMH combined with uncleaved AMH (in 90% human serum), so that all the samples had close to the same level of total AMH. Accordingly, samples were prepared that contained approximately 0, 20, 40, 60, 80, and 100% cleaved AMH. Total AMH levels in these six samples were first measured using the ELISA for total AMH and the results are shown in FIG. 13A, where the experimentally determined levels are compared to the actual levels. The actual levels of total and cleaved AMH in each sample were recalculated using the experimentally determined values for total AMH in the Control 0 (0% cleaved) and Control 100 (100% cleaved) samples, which contained only uncleaved or cleaved AMH, respectively. There was fairly close agreement between the experimental and actual levels of total AMH.

Figure 13B:
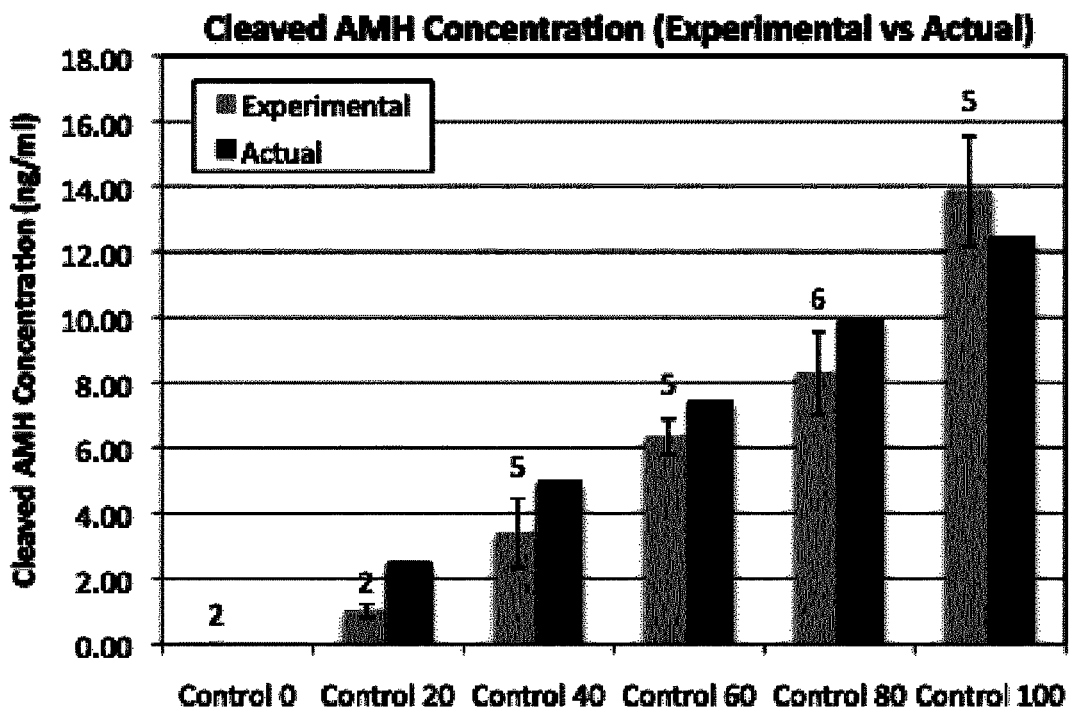
Figure 13C:
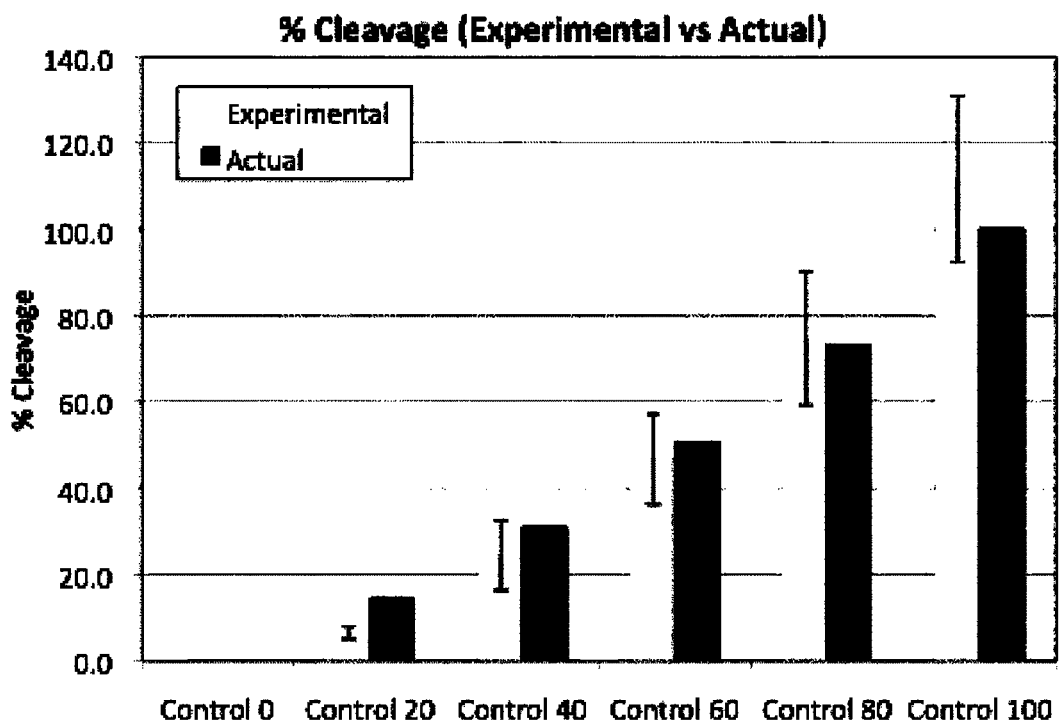

A comparison of the experimentally determined levels of cleaved AMH measured with the cAMH-ELISA with the actual levels of cleaved AMH in each sample is shown in FIG. 13B. As with the total AMH measurements, there was fairly close agreement between the experimental and actual levels of cleaved AMH, although there was a larger difference observed in the sample containing the lowest level of cleaved AMH. By dividing the cleaved AMH level with the total AMH level for each sample (experimental and actual), the level of AMH cleavage (experimental and actual) in each sample can be calculated. As shown in FIG. 13C, the AMH cleavage levels determined experimentally are in fairly close agreement with the actual cleavage levels, with the sample containing the lowest level of AMH cleavage showing the largest divergence. These results show that the cAMH-ELISA can accurately detect the level of cleaved AMH in a sample containing a mixture of cleaved and uncleaved AMH, although accuracy decreases somewhat at low levels of AMH cleavage. The ELISA experiments shown in FIG. 13 were performed with AMH diluted into human serum, indicating that similar measurements should be possible in patient samples.

Measurement of levels of cleaved AMH and AMH cleavage in patient samples. Before using the cAMH-ELISA to measure the level of active cleaved AMH in patient samples, we characterized the forms of AMH in a number of patient samples using a biochemical approach. An anti-N-terminal AMH mAb (10.6), conjugated to Sepharose, was used to capture AMH in patient samples, either serum or follicular fluid. The captured AMH was then analyzed by SDS-PAGE under reducing conditions and western blotting using an anti-AMH polyclonal Ab (L44). The two western blots in FIG. 14 show the analysis of four patient samples; different amounts of protein recovered from the 10.6-Sepharose precipitations were loaded on each western blot to allow better quantitation of AMH processing. Uncleaved and cleaved AMH were run as controls to show the positions of the uncleaved AMH precursor, and the N-terminal pro-region produced after cleavage. The lower band running in the patient samples is human IgG heavy chain, which cross-reacts with the secondary antibody. The N-terminal pro-region band was detected in patient samples 399, 400, and 3, indicating that these samples contain some level of cleaved AMH. Very little or no pro-region band was observed in patient 208, indicating that it contains none or very little active cleaved AMH. Densitometry analysis of these western blots allowed an assessment of the relative levels of the uncleaved precursor and pro-region bands, and therefore a calculation of the level of AMH cleavage, which is shown below the western blots. The patient samples show various levels of AMH cleavage, ranging from 0 to 50%.

In Table 1, the levels of total and cleaved AMH determined using the ELISAs for total and cleaved AMH are shown, along with the calculated levels of AMH cleavage. The level of AMH cleavage determined from the western blots in FIG. 14 are also shown and correlate fairly well with the values determined by ELISA. While patient 399 contains a much lower level of total AMH than patients 400 and 3, it has a relatively high level of cleaved AMH compared to the other patient samples. The close agreement between the levels of AMH cleavage determined by ELISA and the biochemical analysis validates the cAMH-ELISA as an accurate tool for assessing AMH cleavage levels in patient samples.

TABLE 1

Measurement of total and cleaved AMH levels in patient samples.

|  | Patient 399 | Patient 400 | Patient 3 | Patient 208 | Female serum | Male serum |
|---|---|---|---|---|---|---|
| [Total AMH] (ng/ml) (N) | 8.5 ± 0.7 (8) | 28.0 ± 3.3 (4) | 37.6 ± 6.3 (4) | 9.2 ± 1.4 (7) | 1.9 ± 0.3 (6) | 76.0 ± 11 (2) |
| [Cleaved AMH] (ng/ml) (N) | 4.0 ± 0.2 (6) | 3.5 ± 0.6 (5) | 2.3 ± 1.2 (4) | 0.0 (2) | 0.4 ± 0.2 (2) | ND |
| % Cleavage determined from ELISAs | 47.3 ± 4.8 | 12.5 ± 2.7 | 6.2 ± 3.5 | 0.0 | 21.8 ± 11 | ND |
| % Cleavage estimated from biochemical analysis (FIG. 14) | 50.0 | 15.0 | 0.0 | 0.0 | ND | >70 |

Figure 12A:
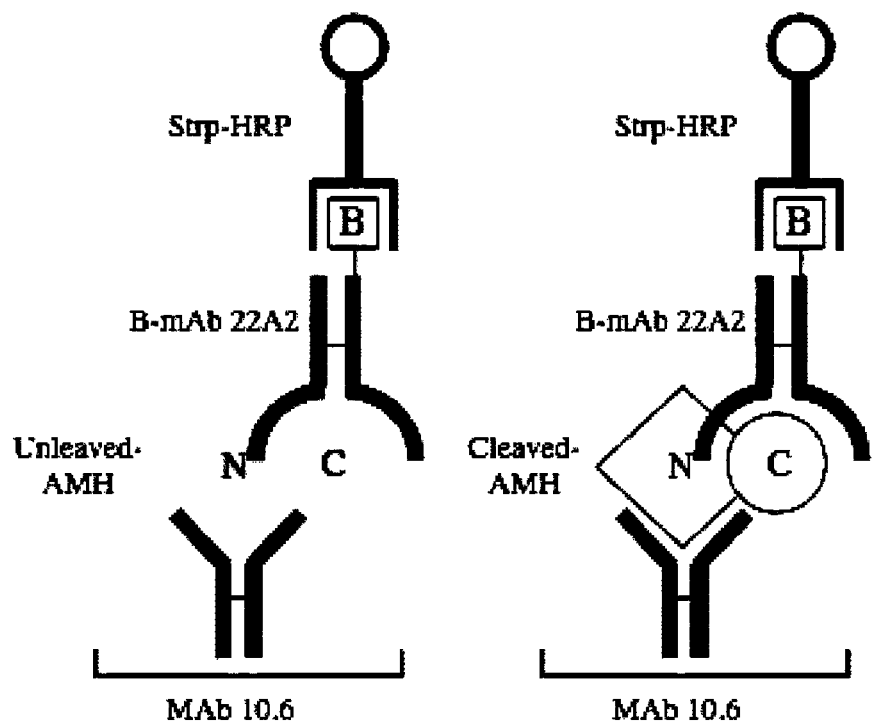
Figure 12B:
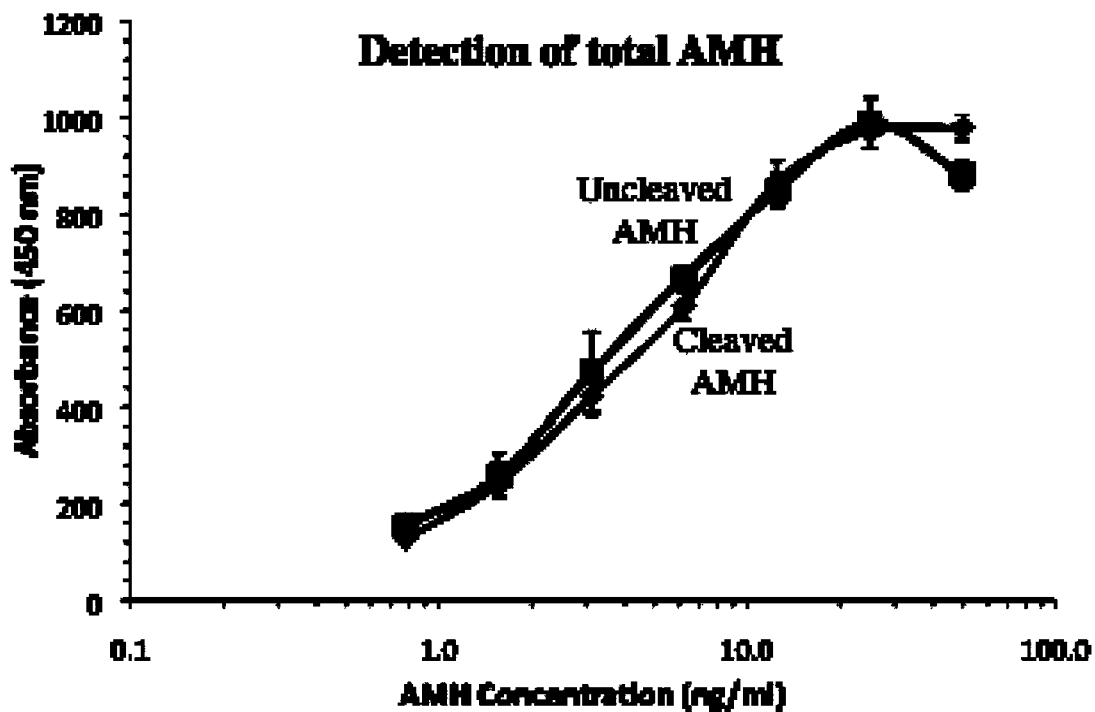
Figure 12C:
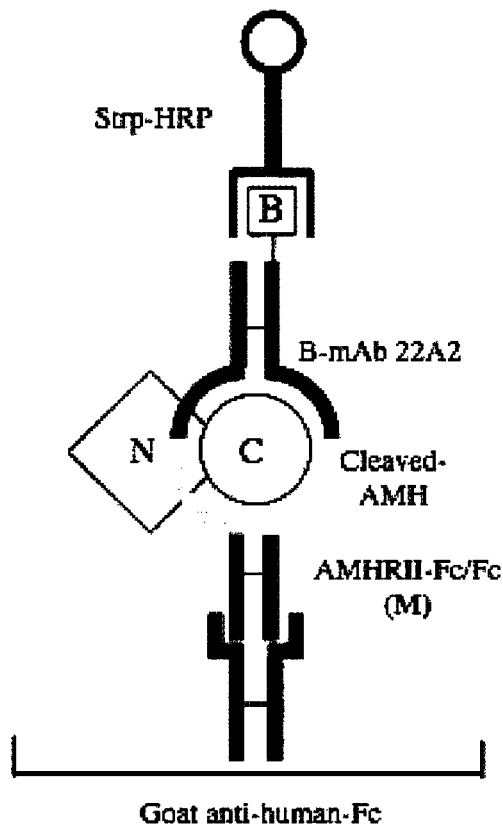
Figure 12D:
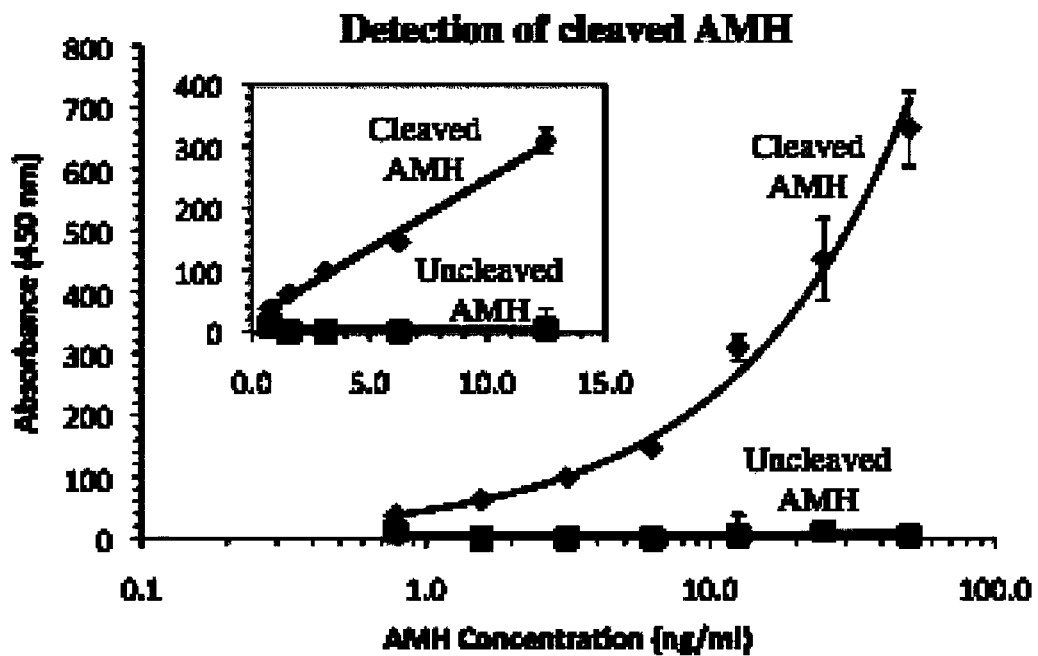

Total AMH Concentrations were determined using the ELISA shown in FIG. 12A. Cleaved AMH concentrations were determined using the cAMH-ELISA shown in FIG. 12B. (N: number of replicates; ND: not done)

REFERENCES

Throughout this application, various references describe the state of the art to which this invention pertains. The disclosures of these references are hereby incorporated by reference into the present disclosure.

1. Josso N, di Clemente N (2003) Transduction pathway of anti-Müllerian hormone, a sex-specific member of the TGF-beta family. Trends Endocrinol Metab 14: 91-97.

2. Broekmans F J, Visser J A, Laven J S, Broer S L, Themmen A P, et al. (2008) Anti-Mülllerian hormone and ovarian dysfunction. Trends Endocrinol Metab 19: 340-347.

3. Masiakos P T, MacLaughlin D T, Maheswaran S, Teixeira J, Fuller A F, Jr., et al. (1999) Human ovarian cancer, cell lines, and primary ascites cells express the human Müllerian inhibiting substance (MIS) type II receptor, bind, and are responsive to MIS. Clin Cancer Res 5: 3488-3499.

4. Gouédard L, Chen Y G, Thevenet L, Racine C, Borie S, et al. (2000) Engagement of bone morphogenetic protein type IB receptor and Smad1 signaling by anti-Müllerian hormone and its type II receptor. J Biol Chem 275: 27973-27978.

5. Massagué J, Seoane J, Wotton D (2005) Smad transcription factors. Genes Dev 19: 2783-2810.

6. Baarends W M, van Helmond M J, Post M, van der Schoot P J, Hoogerbrugge J W, et al. (1994) A novel member of the transmembrane serine/threonine kinase receptor family is specifically expressed in the gonads and in mesenchymal cells adjacent to the Müllerian duct. Development 120: 189-197.

7. di Clemente N, Wilson C, Faure E, Boussin L, Carmillo P, et al. (1994) Cloning, expression, and alternative splicing of the receptor for anti-Müllerian hormone. Mol Endocrinol 8: 1006-1020.

8. di Clemente N, Jamin S P, Lugovskoy A, Carmillo P, Ehrenfels C, et al. (2010) Processing of anti-Müllerian hormone regulates receptor activation by a mechanism distinct from TGF-{beta}. Mol Endocrinol 24: 2193-2206.

9. Sengle G, Ono R N, Lyons K M, Bachinger H P, Sakai L Y (2008) A new model for growth factor activation: type II receptors compete with the prodomain for BMP-7. J Mol Biol 381: 1025-1039.

10. Racine C, Rey R, Forest M G, Louis F, Ferre A, et al. (1998) Receptors for anti-Müllerian hormone on Leydig cells are responsible for its effects on steroidogenesis and cell differentiation. Proc Natl Acad Sci USA 95: 594-599.

11. Durlinger A L, Gruijters M J, Kramer P, Karels B, Kumar T R, et al. (2001) Anti-Mülllerian hormone attenuates the effects of FSH on follicle development in the mouse ovary. Endocrinology 142: 4891-4899.

12. Durlinger A L, Kramer P, Karels B, de Jong F H, Uilenbroek J T, et al. (1999) Control of primordial follicle recruitment by anti-Mülllerian hormone in the mouse ovary. Endocrinology 140: 5789-5796.

13. Arango N A, Kobayashi A, Wang Y, Jamin S P, Lee H H, et al. (2008) A mesenchymal perspective of Müllerian duct differentiation and regression in Amhr2-lacZ mice. Mol Reprod Dev 75: 1154-1162.

14. Lebeurrier N, Launay S, Macrez R, Maubert E, Legros H, et al. (2008) Anti-Müllerian-hormone-dependent regulation of the brain serine-protease inhibitor neuroserpin. J Cell Sci 121: 3357-3365.

15. Wang P Y, Koishi K, McGeachie A B, Kimber M, Maclaughlin D T, et al. (2005) Müllerian inhibiting substance acts as a motor neuron survival factor in vitro. Proc Natl Acad Sci USA 102: 16421-16425.

16. Rey R A, Belville C, Nihoul-Fekete C, Michel-Calemard L, Forest M G, et al. (1999) Evaluation of gonadal function in 107 intersex patients by means of serum anti-Müllerian hormone measurement. J Clin Endocrinol Metab 84: 627-631.

17. La Marca A, Sighinolfi G, Radi D, Argento C, Baraldi E, et al. (2010) Anti-Müllerian hormone (AMH) as a predictive marker in assisted reproductive technology (ART). Hum Reprod Update 16: 113-130.

18. Fallat M E, Siow Y, Marra M, Cook C, Carrillo A (1997) Müllerian-inhibiting substance in follicular fluid and serum: a comparison of patients with tubal factor infertility, polycystic ovary syndrome, and endometriosis. Fertil Steril 67: 962-965.

19. Stubbs S A, Hardy K, Da Silva-Buttkus P, Stark J, Webber L J, et al. (2005) Anti-Müllerian hormone protein expression is reduced during the initial stages of follicle development in human polycystic ovaries. J Clin Endocrinol Metab 90: 5536-5543.

20. Jonard S, Dewailly D (2004) The follicular excess in polycystic ovaries, due to intra-ovarian hyperandrogenism, may be the main culprit for the follicular arrest. Hum Reprod Update 10: 107-117.

21. Bakkum-Gamez J N, Aletti G, Lewis K A, Keeney G L, Thomas B M, et al. (2008) Müllerian inhibiting substance type II receptor (MISIIR): a novel, tissue-specific target expressed by gynecologic cancers. Gynecol Oncol 108: 141-148.

22. Yuan Q A, Simmons H H, Robinson M K, Russeva M, Marasco W A, et al. (2006) Development of engineered antibodies specific for the Müllerian inhibiting substance type II receptor: a promising candidate for targeted therapy of ovarian cancer. Mol Cancer Ther 5: 2096-2105.

23. Salhi I, Cambon-Roques S, Lamarre I, Laune D, Molina F, et al. (2004) The anti-Müllerian hormone type II receptor: insights into the binding domains recognized by a monoclonal antibody and the natural ligand. Biochem J 379: 785-793.

24. Yuan Q A, Robinson M K, Simmons H H, Russeva M, Adams G P (2008) Isolation of anti-MISIIR scFv molecules from a phage display library by cell sorter biopanning Cancer Immunol Immunother 57: 367-378.

25. Long W Q, Ranchin V, Pautier P, Belville C, Denizot P, et al. (2000) Detection of minimal levels of serum anti-Müllerian hormone during follow-up of patients with ovarian granulosa cell tumor by means of a highly sensitive enzyme-linked immunosorbent assay. J Clin Endocrinol Metab 85: 540-544.

26. Kevenaar M E, Meerasahib M F, Kramer P, van de Lang-Born B M, de Jong F H, et al. (2006) Serum anti-mullerian hormone levels reflect the size of the primordial follicle pool in mice. Endocrinology 147: 3228-3234.

27. Kumar A, Kalra B, Patel A, McDavid L, Roudebush W E (2010) Development of a second generation anti-Mullerian hormone (AMH) ELISA. J Immunol Methods 362: 51-59.

The invention claimed is:

1. A soluble monomeric AMHRII fusion protein comprising a first chain having an AMHRII extracellular domain fused to a Fc domain and a second chain having a Fc domain, wherein the first and second chains are disulfide bonded within their Fc domains.

2. The soluble monomeric AMHRII fusion protein of claim 1 which is produced in a eukaryotic cell.

3. The soluble monomeric AMHRII fusion protein of claim 2 wherein the C-terminal end of the AMHRII extracellular domain is fused to the N-terminal end of the Fc domain of the first chain.

4. An eukaryotic host cell which is transformed with a vector comprising a nucleic acid molecule encoding a soluble monomeric AMHRII fusion protein having an AMHRII extracellular domain fused to a Fc domain, and with a vector comprising a nucleic acid molecule encoding a second chain having a single Fc domain.

5. A method for detecting or quantifying the presence of bioactive cleaved AMH in a sample comprising the step of contacting the sample with a soluble monomeric AMHRII fusion protein comprising a first chain having an AMHRII extracellular domain fused to a Fc domain and a second chain having a Fc domain, wherein the chains are disulfide bonded within their Fc domains.

6. The method of claim 5 wherein the sample is a biological sample, or is a body fluid.

7. The method of claim 6, wherein the biological sample is a tissue extract, a cell lysate or culture medium.

8. The method of claim 6, wherein the body fluid is whole blood, serum, plasma, follicular fluid, seminal fluid, synovial fluid, cerebrospinal fluid, saliva, or urine.

9. The method of claim 5 wherein detection or quantification of bioactive cleaved AMH in a sample is achieved with a solid support comprising immobilized soluble monomeric AMHRII fusion protein.

10. The method of claim 9 wherein the immobilized soluble monomeric AMHRII fusion protein is directly immobilized on the support by the Fc domain, which is coated on a surface of the solid support.

11. The method of claim 5 wherein the soluble monomeric AMHRII fusion protein is used in combination with an anti-AMH antibody.

12. The method of claim 11 which comprises the steps of i) providing a solid support coated with an amount of antibodies specific for the Fc domain of the soluble monomeric AMHRII fusion protein, ii) adding an amount of the soluble monomeric AMHRII fusion protein of the invention, iii) bringing the sample containing AMH into contact with the solid support, iv) adding an amount of the anti-AMH antibody which is conjugated to a first label and v) adding an amount of a binding partner which is specific for the label of the AMH-antibody and which is conjugated to a second label wherein while the soluble monomeric AMHRII fusion protein captures bioactive cleaved AMH present in the sample, the anti-AMH antibody binds to the AMH and the binding partner conjugated with the second label binds the first label conjugated to the anti-AMH antibody and wherein, measuring the amount of bound binding partner which is specific for the label of the anti-AMH antibody reveals the amount of bioactive cleaved AMH present in the sample.

13. The method of claim 12 wherein the anti-AMH antibody is directed to an epitope within a C-terminal region of AMH, which does not prevent interaction between the bioactive cleaved AMH and the extra-cellular domain of AMHRII of the fusion protein.

14. The method of claim 13 wherein the first label is biotin and the binding partner is streptavidin conjugated with horseradish peroxidase (HRP).

15. The method of claim 13 further comprising washing reactants with a buffer after one or more of steps i), ii), iii), iv), and v).

16. The method of claim 15, wherein the buffer is phosphate buffered saline (PBS).

17. A diagnostic method for determining the fertility of a subject or for diagnosing and/or monitoring the presence of a cancer in a subject in need thereof, said method comprising quantifying bioactive cleaved AMH in a sample obtained from said subject by contacting the sample with a soluble monomeric AMHRII fusion protein comprising a first chain having an AMHRII extracellular domain fused to a Fc domain and a second chain having a Fc domain, wherein the chains are disulfide bonded within their Fc domains.

18. The diagnostic method of claim 17 which comprises the steps of i) providing the sample obtained from the subject, ii) contacting the sample with the soluble monomeric AMHRII fusion protein, wherein the step of contacting is performed under conditions appropriate for formation of a complex between the soluble monomeric AMHRII fusion protein and bioactive cleaved AMH present in the sample, iii) quantifying an amount of complexes formed to determine the amount of bioactive cleaved AMH present in the sample, and iv) correlating the amount of bioactive cleaved AMH with the determination of the fertility of a subject or with the diagnosis and/or the monitoring of a cancer.

19. A kit for detecting or quantifying the presence of bioactive cleaved AMH in a sample, comprising a soluble monomeric AMHRII fusion protein comprising a first chain having an AMHRII extracellular domain fused to a Fc domain and a second chain having a Fc domain, wherein the chains are disulfide bonded within their Fc domains.

20. The kit of claim 19 which also comprises an anti-AMH antibody labelled with biotin, a solid support coated with anti-Fc domain antibodies, and a streptavidin binding partner conjugated with HRP.

21. A method for improving female fertility and/or for treating female infertility disorders and/or for improving or treating male infertility in a subject in need thereof, comprising
administering to the subject an effective amount of a soluble monomeric AMHRII fusion protein comprising a first chain having an AMHRII extracellular domain fused to a Fc domain and a second chain having a Fc domain, wherein the chains are disulfide bonded within their Fc domains.

22. A pharmaceutical composition comprising a soluble monomeric AMHRII fusion protein comprising a first chain having an AMHRII extracellular domain fused to a Fc domain and a second chain having a Fc domain, wherein the chains are disulfide bonded within their Fc domains.

* * * * *